United States Patent [19]
Panescu et al.

[11] Patent Number: 6,053,912
[45] Date of Patent: *Apr. 25, 2000

[54] SYSTEMS AND METHODS FOR SENSING SUB-SURFACE TEMPERATURES IN BODY TISSUE DURING ABLATION WITH ACTIVELY COOLED ELECTRODES

[75] Inventors: Dorin Panescu, Sunnyvale; David K. Swanson, Mountain View; Sidney D. Fleischman, Menlo Park; Thomas M. Bourne, Mountain View, all of Calif.

[73] Assignee: EP Techonologies, Inc., Sunnyvale, Calif.

[ * ] Notice: This patent is subject to a terminal disclaimer.

[21] Appl. No.: 08/942,321

[22] Filed: Oct. 1, 1997

Related U.S. Application Data

[63] Continuation of application No. 08/431,857, May 1, 1995, abandoned.

[51] Int. Cl.$^7$ ................................................. A61B 17/32
[52] U.S. Cl. ................................. 606/40; 606/34; 606/38; 606/42; 606/49; 606/31; 607/99; 607/102; 607/104; 607/105; 607/113
[58] Field of Search ................. 606/29–52; 607/98–104, 607/109–120

[56] References Cited

U.S. PATENT DOCUMENTS

| | | |
|---|---|---|
| 4,860,744 | 8/1989 | Johnson et al. . |
| 4,950,267 | 8/1990 | Ishihara et al. ........................... 606/12 |
| 5,073,167 | 12/1991 | Carr et al. . |
| 5,330,518 | 7/1994 | Neilson et al. . |
| 5,334,193 | 8/1994 | Nardella . |
| 5,348,554 | 9/1994 | Imran et al. . |
| 5,383,876 | 1/1995 | Nardella . |
| 5,423,811 | 6/1995 | Imran et al. . |
| 5,431,649 | 7/1995 | Mulia et al. ............................. 607/120 |
| 5,456,682 | 10/1995 | Edwards et al. . |
| 5,480,417 | 1/1996 | Hascoet et al. . |
| 5,688,267 | 11/1997 | Panescu et al. ......................... 607/102 |
| 5,702,386 | 12/1997 | Stern et al. ............................... 606/45 |
| 5,735,846 | 4/1998 | Panescu et al. ........................... 606/41 |
| 5,743,903 | 4/1998 | Stern et al. ............................... 606/42 |
| 5,755,715 | 5/1998 | Stern et al. ............................... 606/42 |
| 5,797,905 | 8/1998 | Fleischmann et al. ................... 606/41 |
| 5,800,432 | 9/1998 | Swanson ................................... 606/42 |
| 5,853,409 | 12/1998 | Swanson et al. ....................... 600/549 |

FOREIGN PATENT DOCUMENTS

| | | | |
|---|---|---|---|
| 0 608 609 A2 | 3/1994 | European Pat. Off. | ........ A61B 17/39 |
| 9315664 | 8/1993 | WIPO | ...................................... 606/10 |
| WO 94/10922 | 5/1994 | WIPO | ............................. A61B 17/36 |

*Primary Examiner*—David M. Shay
*Attorney, Agent, or Firm*—Lyon & Lyon LLP

[57] ABSTRACT

Systems and associated methods for ablating body tissue employ an electrode for contacting tissue to form a tissue-electrode interface. The electrode is adapted to be connected to a source of ablation energy to conduct ablation energy for transmission by the electrode into tissue at the tissue-electrode interface. The systems and methods also include an element to cool the electrode. The systems and methods hold a tissue temperature sensing element in a carrier in thermal conductive contact with tissue beneath the tissue-electrode interface. The systems and methods include a controller that is coupled to the tissue temperature sensing element to control either the supply of ablation energy, or the rate at which the electrode is cooled, or both based, at least in part, upon temperature sensed by the temperature sensing element.

41 Claims, 20 Drawing Sheets

LESION VOLUME INCREASE
VS.
ELECTRODE TEMPERATURE
(MAXIMUM TISSUE TEMPERATURE AT 94°C)

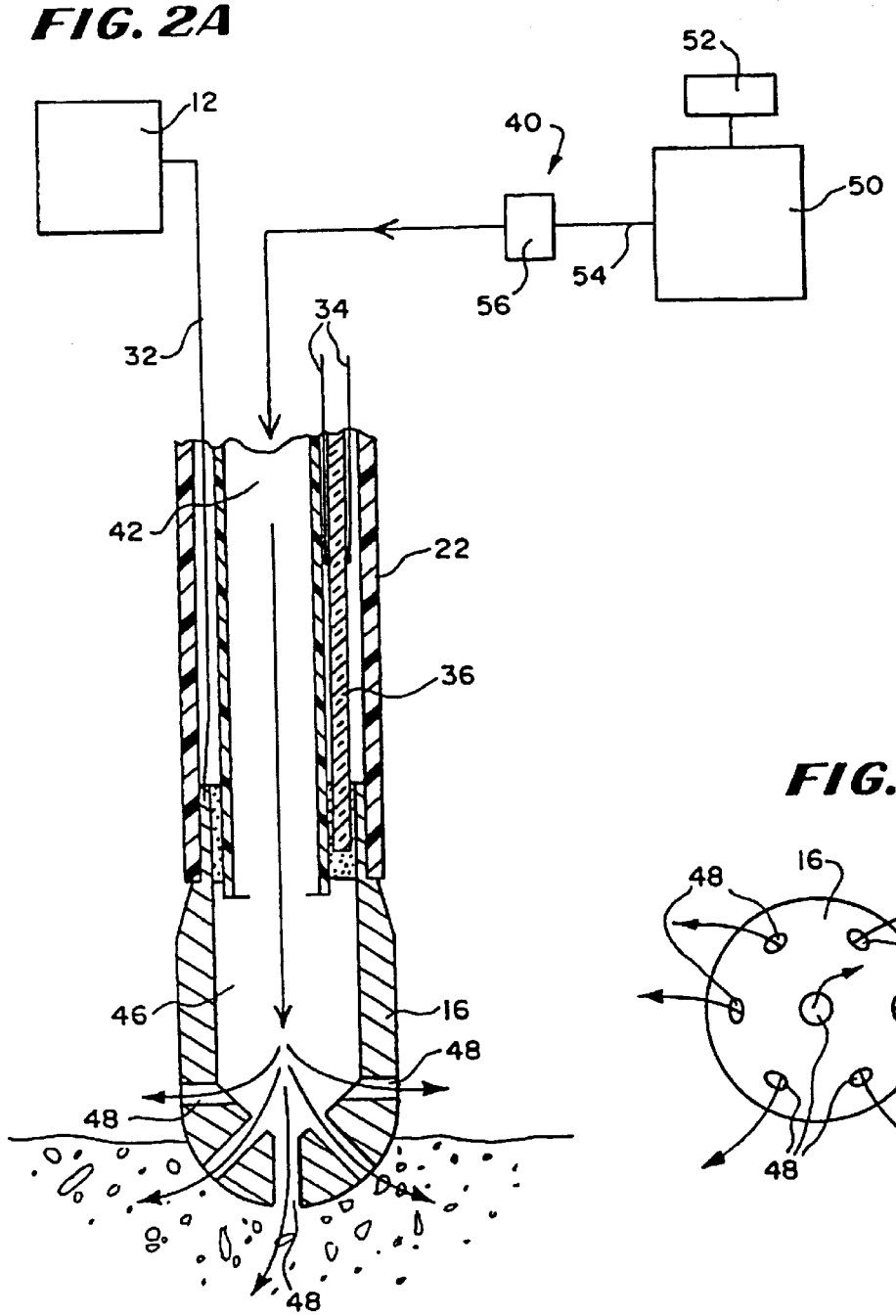

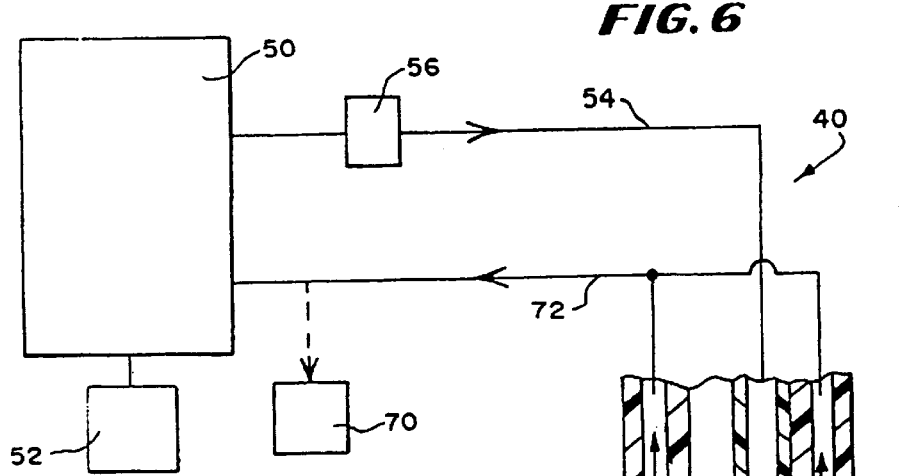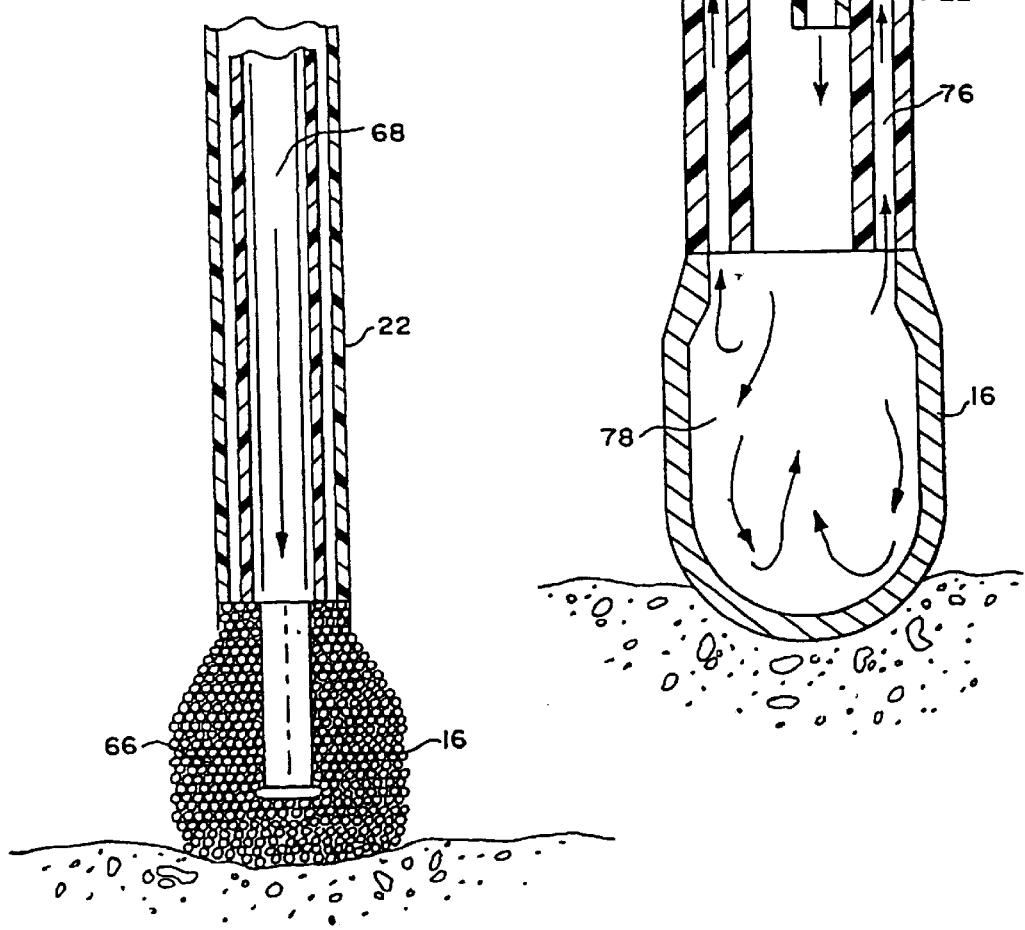

FIG. 13
FIG. 14
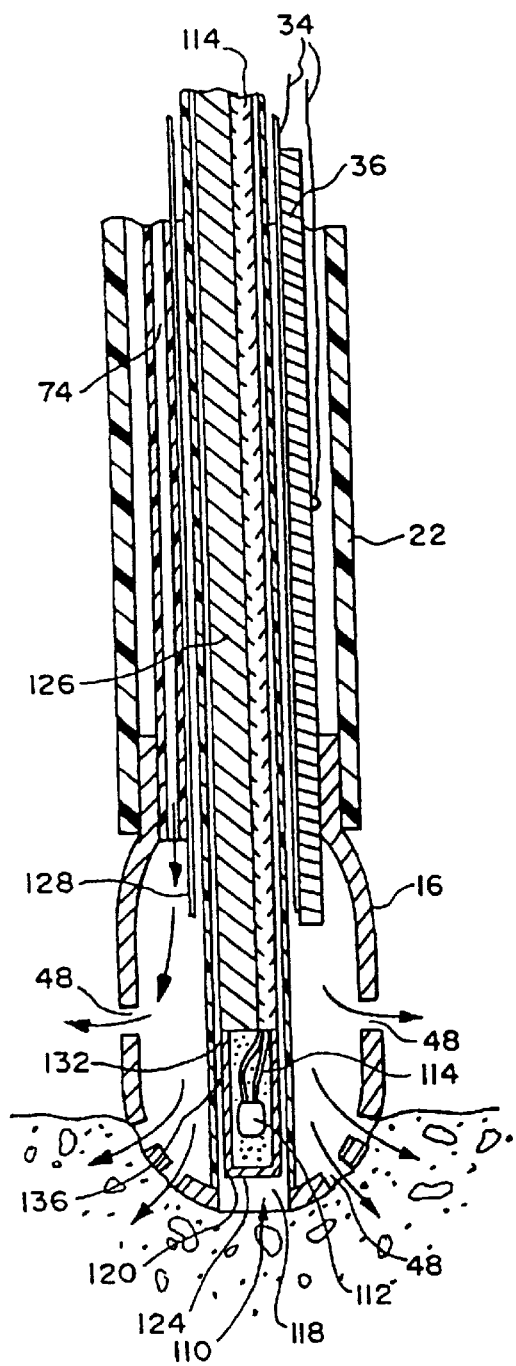
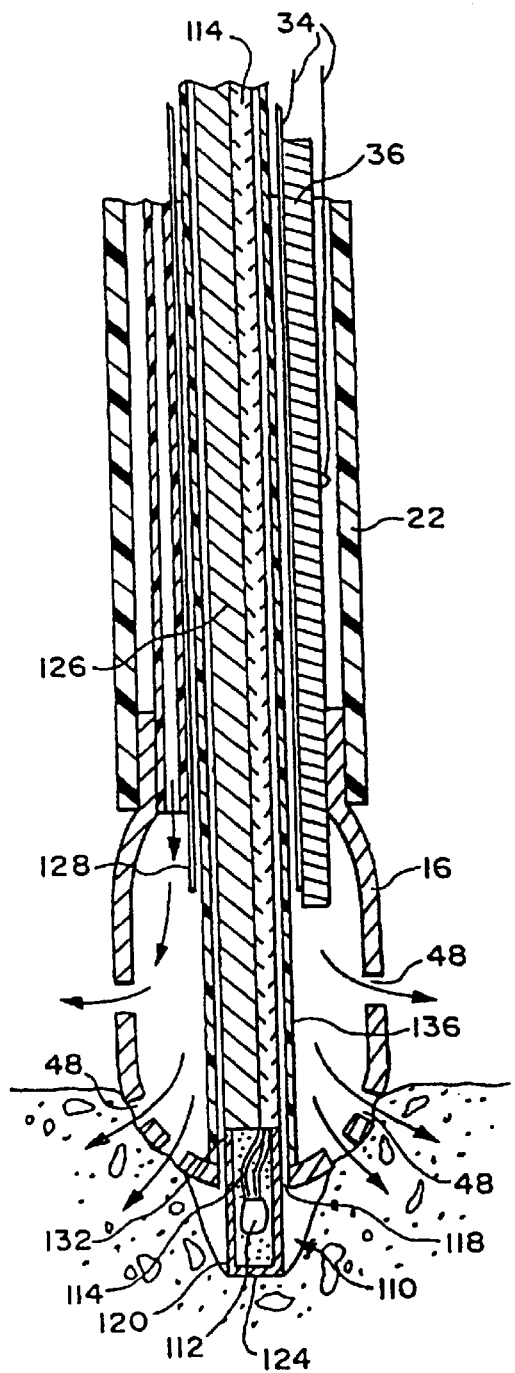

6,053,912

SYSTEMS AND METHODS FOR SENSING SUB-SURFACE TEMPERATURES IN BODY TISSUE DURING ABLATION WITH ACTIVELY COOLED ELECTRODES

This is a continuation of application(s) Ser. No. 08/431,857 filed on May 1, 1995, now abandoned.

FIELD OF THE INVENTION

In a general sense, the invention is directed to systems and methods for creating lesions in the interior regions of the human body. In a more particular sense, the invention is directed to systems and methods for ablating heart tissue for treating cardiac conditions.

BACKGROUND OF THE INVENTION

Physicians frequently make use of catheters today in medical procedures to gain access into interior regions of the body. In some procedures, the catheter carries an energy transmitting element on its distal tip to ablate body tissues.

In such procedures, the physician must establish stable and uniform contact between the energy transmitting element and the tissue to be ablated. Upon establishing contact, the physician must then carefully apply ablating energy to the element for transmission to the tissue.

The need for precise control over the emission of ablating energy is especially critical during catheter-based procedures for ablating heart tissue. These procedures, called electrophysiology therapy, are becoming increasingly more widespread for treating cardiac rhythm disturbances, called arrhythmias. Cardiac ablation procedures typically use radio frequency (RF) energy to form a lesion in heart tissue.

The principal objective of the invention is to provide systems and methods for monitoring and reliably controlling the application of energy to ablate body tissue, thereby providing therapeutic results in a consistent and predictable fashion.

SUMMARY OF THE INVENTION

The invention provides systems and methods that provide reliable control over tissue heating and ablation procedures using temperature sensing.

One aspect of the invention provides systems and associated methods for ablating body tissue. The systems and methods employ an electrode for contacting tissue to form a tissue-electrode interface. The electrode is adapted to be connected to a source of ablation energy to conduct ablation energy for transmission by the electrode into tissue at the tissue-electrode interface. The systems and methods also include an element to cool the electrode. The systems and methods hold a tissue temperature sensing element in a carrier in thermal conductive contact with tissue beneath the tissue-electrode interface.

According to another aspect of the invention, the systems and methods include a controller that is coupled to the tissue temperature sensing element to control the supply of ablation energy based, at least in part, upon temperature sensed by the temperature sensing element.

According to another aspect of the invention, the systems and methods include a controller that is coupled to the tissue temperature sensing element to control the rate at which the electrode is cooled based, at least in part, upon temperature sensed by the temperature sensing element.

In a preferred embodiment, the carrier holds the tissue temperature sensing element in thermal conductive contact with tissue, while keeping the temperature sensing element in isolation from the thermal conductive contact with the electrode. The carrier has prescribed thermal conductive characteristics that significantly improve the sensitivity of the temperature sensing element to tissue temperature and not the temperature of the electrode.

In a preferred embodiment, the systems and methods move the carrier into and out of thermal conductive contact with tissue beneath the tissue-electrode interface.

Other features and advantages of the inventions are set forth in the following Description and Drawings, as well as in the appended claims.

BRIEF DESCRIPTION OF THE DRAWINGS

FIG. 2A is a side section view of an actively cooled electrode of the open system variety that can be used in the system shown in FIG. 1A;

FIG. 2B is a section view of the end of the actively cooled electrode shown in FIG. 2A;

FIG. 5 is a side section view of another actively cooled electrode of the open system variety that can be used in the system shown in FIG. 1A;

FIG. 6 is a side section view of an actively cooled electrode of the closed system variety that can be used in the system shown in FIG. 1A;

FIG. 13 is a side section view of an actively cooled energy transmitting electrode that can be associated with the system shown in FIG. 1A, showing a movable temperature sensing element carried within a heat conducting cap by the electrode, the sensing element being shown in its retracted position within the electrode;

FIG. 14 is a side section view of the energy transmitting electrode shown in FIG. 13, showing the movable temperature sensing element in its extended position projecting into tissue;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1A:
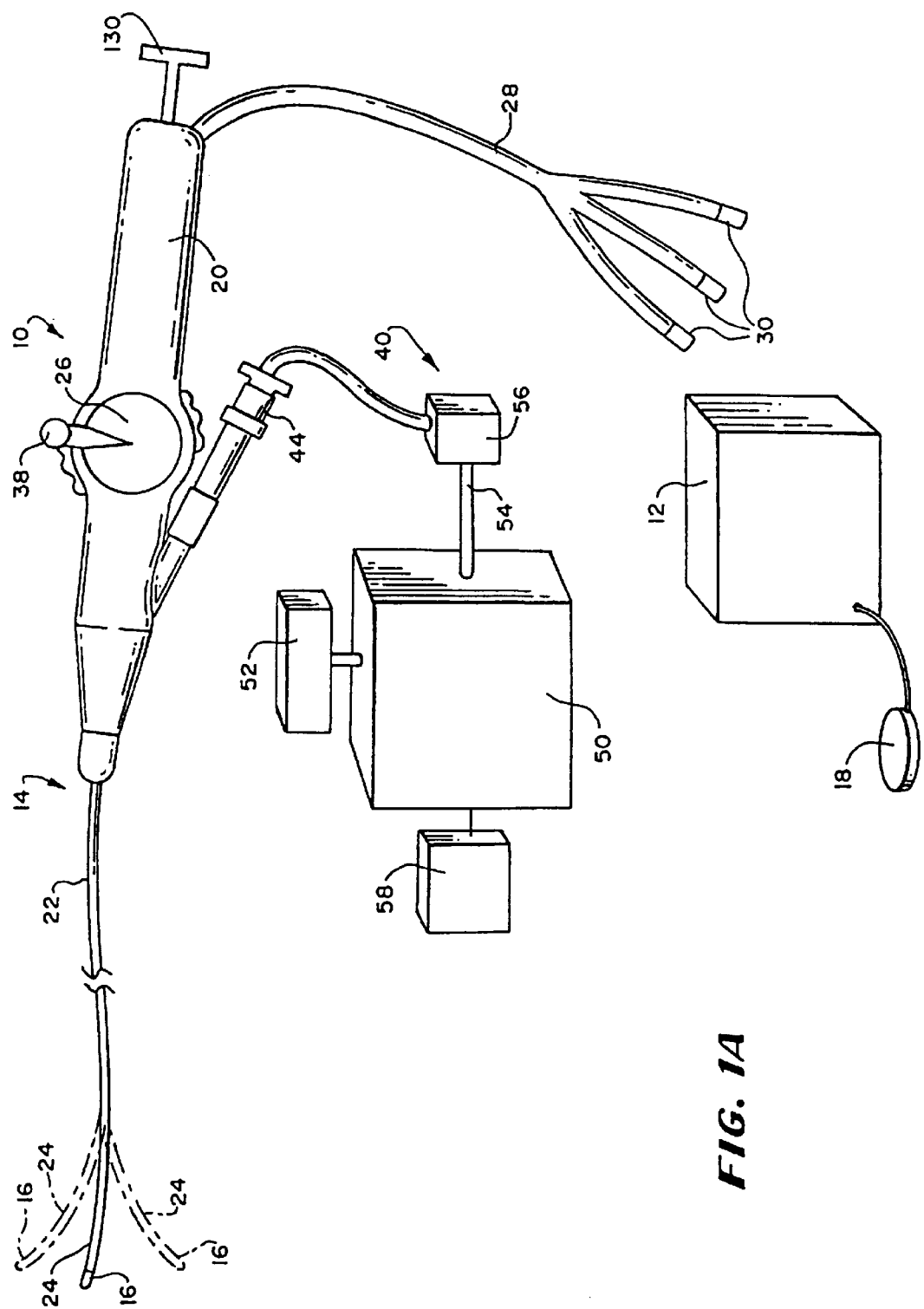
FIG. 1A is a system for ablating tissue using an actively cooled ablation electrode and associated cooling medium delivery system that embodies the features of the invention.

FIG. 1A shows a system 10 for ablating human tissue that embodies the features of the invention.

In the illustrated and preferred embodiment, the system 10 includes a generator 12 that delivers radio frequency energy to ablate tissue. Of coarse, other types of energy can be generated for tissue ablating purposes.

The system 10 also includes a steerable catheter 14 carrying a radio frequency transmitting ablation electrode 16. In the illustrated embodiment, the ablation electrode 16 is made of platinum/iridium. The ablation electrode 16 can be made from other energy transmitting materials like, for example, stainless steel, gold, or silver.

In the illustrated embodiment, the system 10 operates in a unipolar mode. In this arrangement, the system 10 includes a patch electrode that serves as an indifferent electrode 18. In use, the indifferent electrode 18 attaches to the patient's back or other exterior skin area.

Alternatively, the system 10 can be operated in a bipolar mode. In this mode, the catheter 14 carries both electrodes.

The system 10 can be used in many different environments. This specification describes the system 10 when used to provide cardiac ablation therapy.

When used for this purpose, a physician steers the catheter 14 through a main vein or artery (typically the femoral vein or artery) into the interior region of the heart that is to be treated. The physician then further manipulates the catheter 14 to place the electrode 16 into contact with the tissue within the heart that is targeted for ablation. The user directs radio frequency energy from the generator 12 into the electrode 16 to ablate and form a lesion on the contacted tissue.

I. THE ABLATION CATHETER

In the embodiment shown in FIG. 1A, the catheter 14 includes a handle 20, a flexible catheter body 22, and a catheter distal section 24, which carries the electrode 16.

The handle 20 encloses a steering mechanism 26 for the catheter tip 24. A cable 28 extending from the rear of the handle 20 has plugs 30. Some of the plugs 30 are coupled to a signal wire 32(see FIG. 2A) that extends from the ablation electrode 16 through the catheter body 22. The plugs 30 connect to the generator 12 for conveying radio frequency energy to the ablation electrode 16 through the wire 32.

Left and right steering wires 34 (also see FIG. 2A) extend through the catheter body 22 to interconnect the steering mechanism 26 in the handle 20 to the left and right sides of a deflecting spring element 36. Rotating a steering lever 38 on the handle to the left causes the steering mechanism 26 to pull on the left steering wire, causing the spring element 36 to bend to the left (as shown in phantom lines in FIG. 1A). Similarly, rotating the steering lever 38 to the right causes the steering mechanism 26 to pull on the right steering wire 34, causing the spring element 36 to bend to the right (as also shown in phantom lines in FIG. 1A). In this way, the physician steers the ablation electrode 16 into contact with the tissue to be ablated.

Further details of this and other types of steering mechanisms for the ablating element 10 are shown in Lundquist and Thompson U.S. Pat. No. 5,254,088, which is incorporated into this Specification by reference.

A. Actively Cooled Electrodes

Figure 1B:
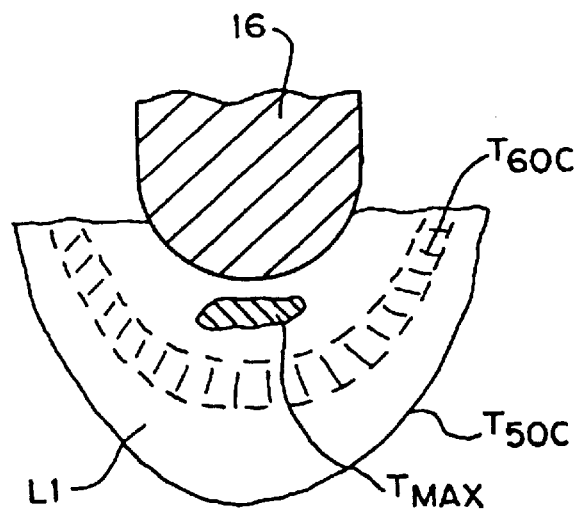
FIG. 1B is a diagrammatic view of a lesion profile, without an actively cooled ablation electrode.
Figure 1C:
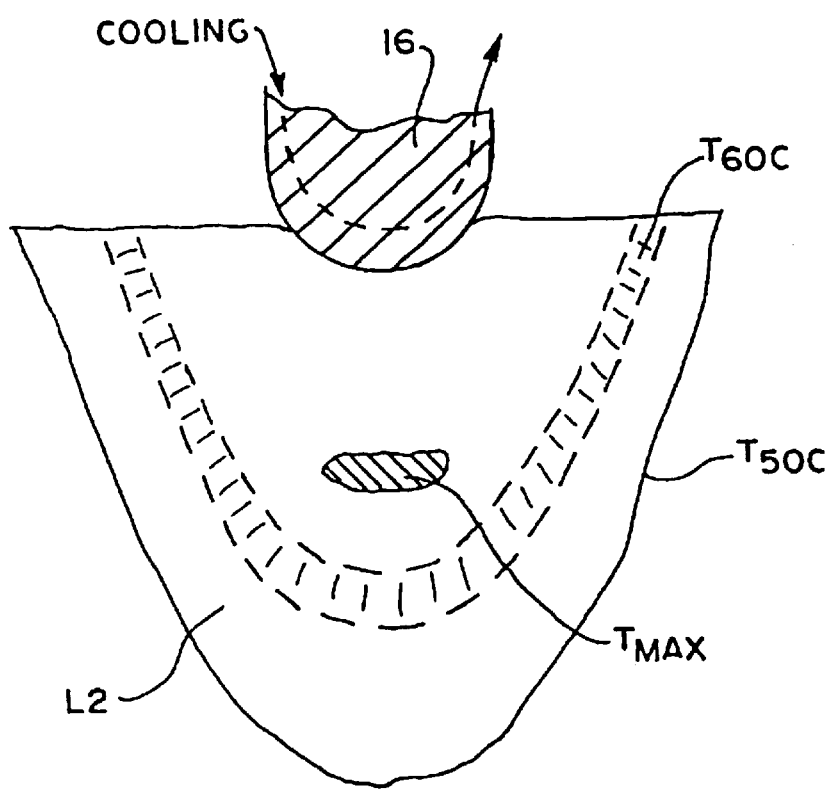
FIG. 1C is a diagrammatic view of a lesion profile, with an actively cooled ablation electrode.

In the illustrated and preferred embodiment, the system 10 includes an assembly 40 for actively cooling the electrode 16. Cooling forces the electrode-tissue interface to lower temperature values, As a result (as FIGS. 1B and 1C show), the hottest iso-thermal region $T_{MAX}$ is shifted deeper into the tissue. This, in turn, shifts the 50° C. iso-thermal region (designated $T_{50C}$), which determines the boundary of the tissue rendered nonviable by ablation, deeper into the tissue. An electrode that is actively cooled can be used to transmit more ablation energy into the tissue, compared to the same electrode that is not actively cooled. As a comparison of FIGS. 1B and 1C shows, the net result is that, with cooling, the lesion (designated L1 and L2, respectively, in FIGS. 1B and 1C) extends deeper into the tissue and has a larger volume.

Figure 1D:
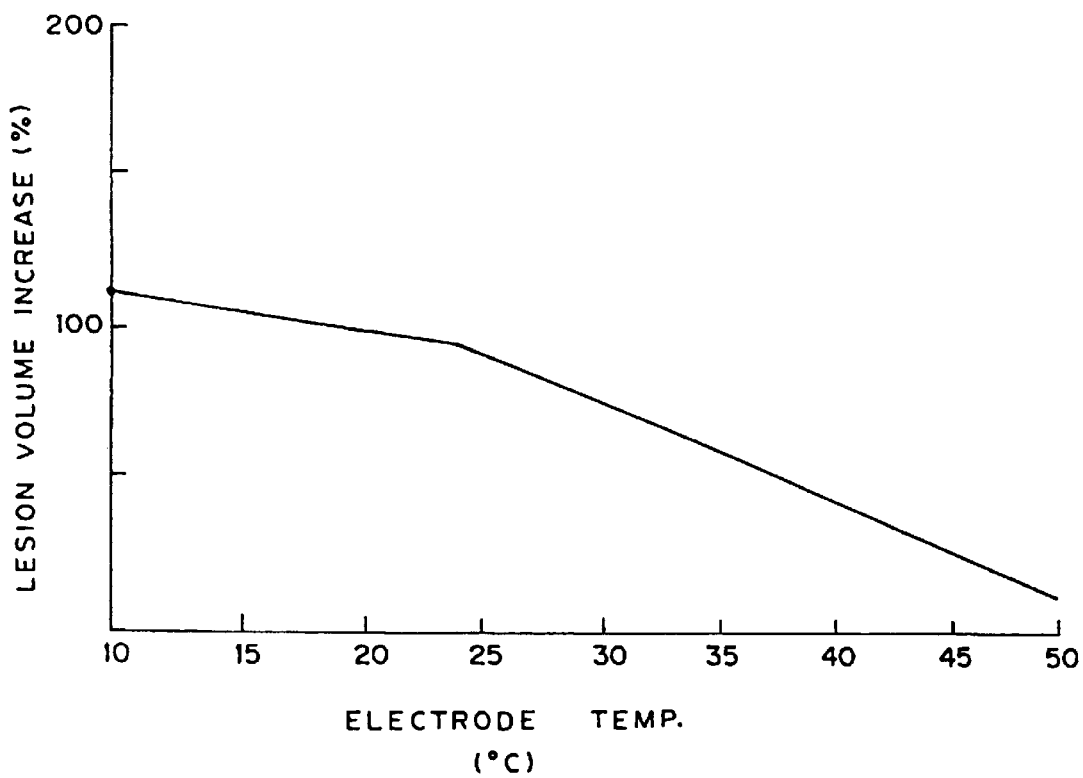
FIG. 1D is a graph showing the increase in lesion volume as a function of the cooling temperature of the ablation electrode.

FIG. 1D shows this effect graphically. Assuming a maximum tissue temperature $T_{MAX}$ of about 94° C., actively cooling the electrode to an electrode temperature T1 below about 35° C. leads to at least a 50% increase in lesion volume. At an electrode temperature T1 below about 25° C., lesion volumes increase by about 100%, i.e., lesion volumes double in size.

There are various ways to structurally provide an electrode that can be actively cooled during use.

1. Open Loop Cooling

In the embodiment shown in FIGS. 2A and 2B, the catheter body 22 includes an interior lumen 42. The proximal end of the lumen communicates with a connection port 44 in the handle (see FIGS. 1A and 15A). The distal end of the lumen 42 communicates with a hollow cavity 46 formed in the electrode 16.

In the illustrated and preferred embodiment, the cavity 46 includes an array of outlet apertures 48 clustered at the distal tip of the electrode 16. Alternatively, a single centrally located outlet aperture, or other arrangements of one or more apertures, could be provided in the distal tip of the electrode 16.

In this arrangement, the cooling assembly 40 includes a source 50 (see FIG. 1A also) of a biocompatible medium, such as saline, with or without heparin. A mechanism 52 cools the medium source 50 to a desired temperature. A supply line 54 with an in-line pump 56 supplies the cooled medium to the connection port 44 on the handle 20. The cooled medium flows through the lumen 42 and into the electrode cavity 46. The outlet apertures 48 discharge the cooled medium into the region surrounding the electrode, as FIG. 2A shows. Because the cooling medium is discharged directly into the space surrounding the electrode 16, this arrangement will be called "open" loop cooling.

The flow of cooling liquid through the electrode cavity 46 conveys heat away from the thermal mass of the electrode 16 by conductive and convective cooling. The system further includes a controller 58 (see FIG. 1A) for controlling the rate of cooling, as will be described in greater detail later.

Preferably, the flow of media through the outlet apertures 48 is sufficient to sustain a positive fluid pressure throughout use, thereby preventing clotting about the electrode 16. The size and number of outlet apertures 48 determine the magnitude of the flow resistance through the electrode 16.

The orientation of the outlet apertures 48 also affects the efficiency of the cooling effect. Preferably, the outlet apertures 48 are clustered at the distal end of the electrode 16, as FIGS. 2A and 2B show. This orientation directs the cooling medium through the entire length of the electrode 16 for better cooling effect. The discharged cooling medium also flows directly into and through the electrode-tissue interface, causing direct cooling of the tissue area being ablated. The direct cooling can reduce the incidence of charring.

Figure 3A:
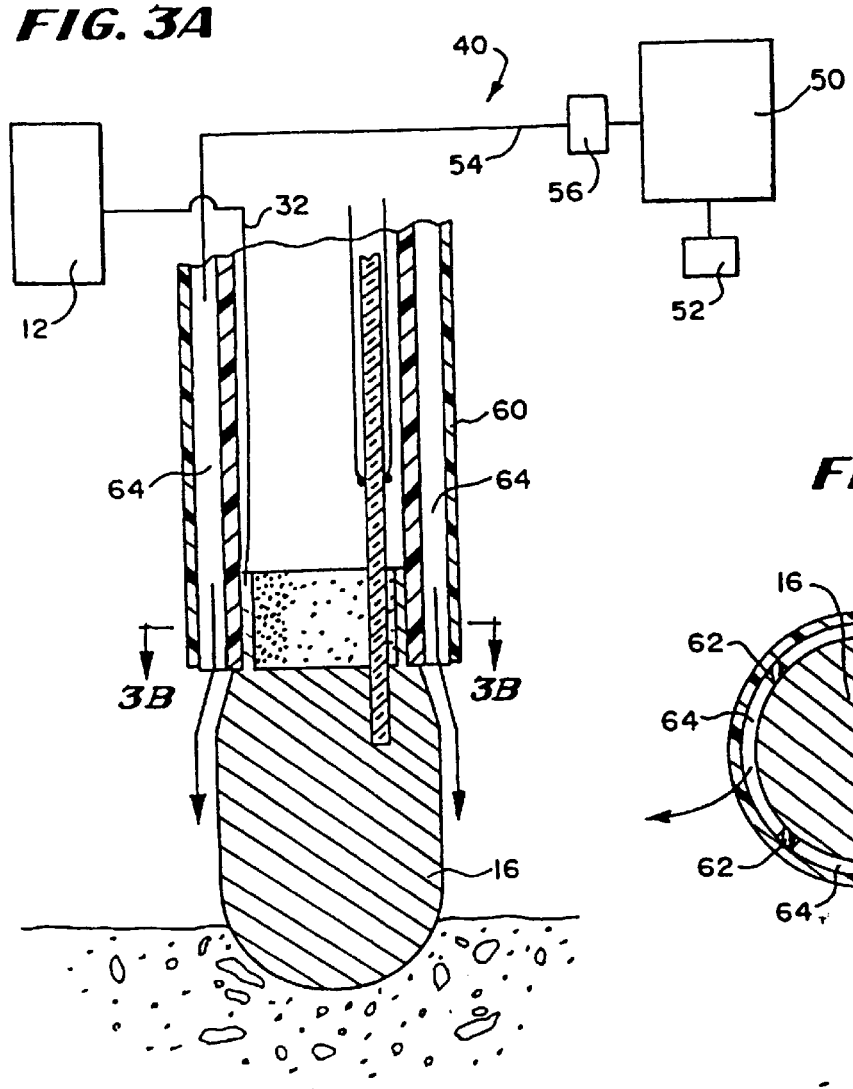
FIG. 3A is a side section view of another actively cooled electrode of the open system variety that can be used in the system shown in FIG. 1A.
Figure 3B:
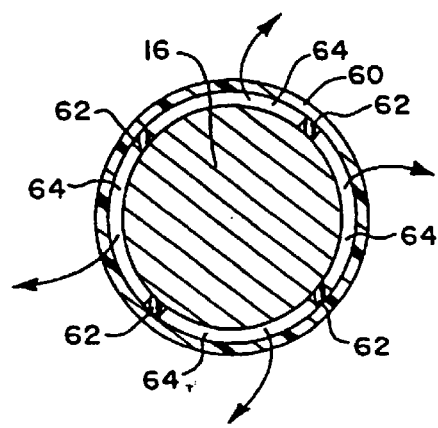
FIG. 3B is a section view of the end of the actively cooled electrode shown in FIG. 3A taken generally along line 3B—3B in FIG. 3A.

FIGS. 3A and 3B show an alternative structural embodiment of an actively cooled electrode of an "open" loop type. In this embodiment, an exterior sleeve 60 surrounds the catheter body 22, forming a circumferential space. The space is compartmentalized by dividers 62 (see FIG. 3B) into multiple, circumferentially spaced lumens 64. Of coarse, the number of lumens 64 can vary.

The proximal end of the sleeve 60 communicates with the connection port 44 on the handle 20. The lumens 64 simultaneously conduct cooling medium supplied to the connection port 44 by the source 50 via the supply line 54 and in-line pump 56. The distal end of the sleeve 60 opens along the exterior sidewall of the electrode 16. There, the lumens 64 discharge the cooling medium along the periphery of the electrode 16 to cool it.

Alternatively, the sleeve 60 can be made to be moved axially along the catheter body 22 like an introducer sheath. In this arrangement, the position of the slidable sleeve can be adjusted to achieve optimal outflow of cooling medium about the electrode.

Figure 4:
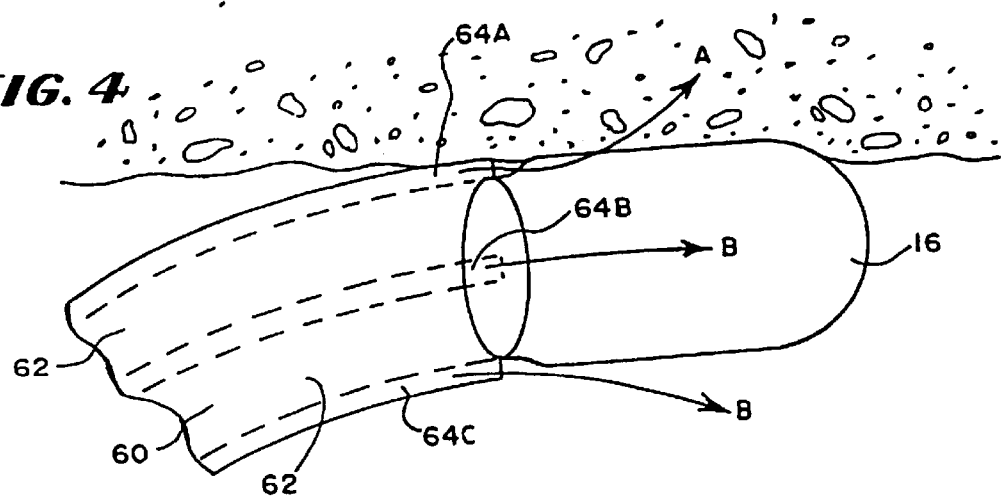
FIG. 4 is a diagrammatic view of an actively cooled electrode like that shown in FIG. 3A in contact with tissue and with different types of medium being conveyed out of the cooling lumens.

Optionally, as FIG. 4 shows, the multiple lumens 64 formed within the exterior sleeve 60 can conduct media having different characteristics benefiting the ablation process. For illustrative purposes, FIG. 4 shows three lumens, designated 64A, 64B, and 64C. The lumen 64A adjacent the region of the electrode 16 in most intimate contact with tissue conducts a hypertonic liquid A having a relatively low resistivity at, for example, about 15 ohm·cm, compared to resistivity of blood, which is about 150 ohm·cm. The hypertonic liquid A discharged in this region therefore improves the transmission of RF energy from the electrode 16 into the tissue, regardless of whether or not the electrode 16 is also actually cooled by the liquid in the process. The other lumens 64B and 64C adjacent the region of the electrode 16 exposed to the blood pool can conduct another liquid B having a relatively high resistivity, compared to blood, of, for example, about 1500 ohm·cm. The liquid B could comprise, for example, a 5% dextrose solution. The liquid B therefore reduces the transmission of RF energy from the electrode 16 into the blood pool, again regardless of whether liquid B also cools the electrode 16 in the process. Furthermore, heparin could be supplied with liquid A through the lumen 64A adjacent the tissue-contacting region of the electrode 16 to locally reduce the incidence of clotting, while no heparin is supplied through the lumens 64B and 64C adjacent the blood-pool exposed region of the electrode 16. In this way, the volume of anticoagulant introduced into the blood pool can be more locally directed and controlled.

FIG. 5 shows another alternative embodiment of an actively cooled electrode of the "open" loop type. In this embodiment, the electrode 16 comprises a foam body 66 of an open cell porous material coated with an electrically conductive substance. The electrically conductive substance can be coated on the porous material 66 using, for example conventional ion beam assisted deposition (IBAD), or similar vapor deposition techniques.

Coated foam body 66 is molded to assume what can be called a normal shape. In the illustrated embodiment (as FIG. 5 shows), the normal uncompressed shape is generally spherical. However, the original uncompressed shape can be rectangular, square, oval, toroid, or virtually any other shape. Due to its porous, open structure, the body 66 can be collapsed, without damage, by an external compression force during deployment in a guide tube (not shown) into another more compact shape.

As in the FIGS. 2A/B embodiment, an interior lumen 68 supplies cooling medium to the porous material of the body 66 from an external source 50 (not shown in FIG. 5). The porous material of the body 66 uniformly perfuses the cooling medium from the lumen 68 for discharge at the surface of the medium.

2. Closed Loop Cooling

FIG. 6 shows an embodiment of electrode 16 that is actively cooled in a "closed" loop manner. During "closed" loop cooling, the cooling medium is not discharged outside the electrode 16 at the ablation site. Instead, the cooling medium is circulated back to the source 50 or to waste 70 away from the ablation site.

In this arrangement, the system includes, in addition to the previously described source 50, supply line 54, and pump 56, a return line 72 that conveys medium away from the electrode 16. The catheter body 22 includes an interior supply lumen 74 and an interior discharge lumen 76. The proximal ends of the lumens 74 and 76 communicate with the connection port 44 on the handle 20, with the supply lumen 74 in communication with the supply line 54 and the discharge lumen 76 in communication with the return line 72.

The distal ends of the lumens 74 and 76 communicate with a hollow cavity 78 formed in the electrode 16. The supply line 54 supplies the cooled medium through the supply lumen 74 into the cavity 78, while the return line 72 returns the medium through the discharge lumen 76 to the medium source 50 or to waste 70. As before, the flow of cooling liquid through the electrode cavity 78 conveys heat away from the thermal mass of the electrode by conductive and convective cooling.

In a "closed" loop arrangement, a pressurized gas could be used as the cooling medium. The pressurized gas would be allowed to expand within the electrode chamber, cooling the electrode by the Joule-Thompson effect. The use of a pressurized gas and the Joule-Thompson effect to cool an electrode is disclosed in Jackson et al. U.S. Pat. No. 5,281,217, which is incorporated herein by reference.

3. Diode Cooling

Figure 7:
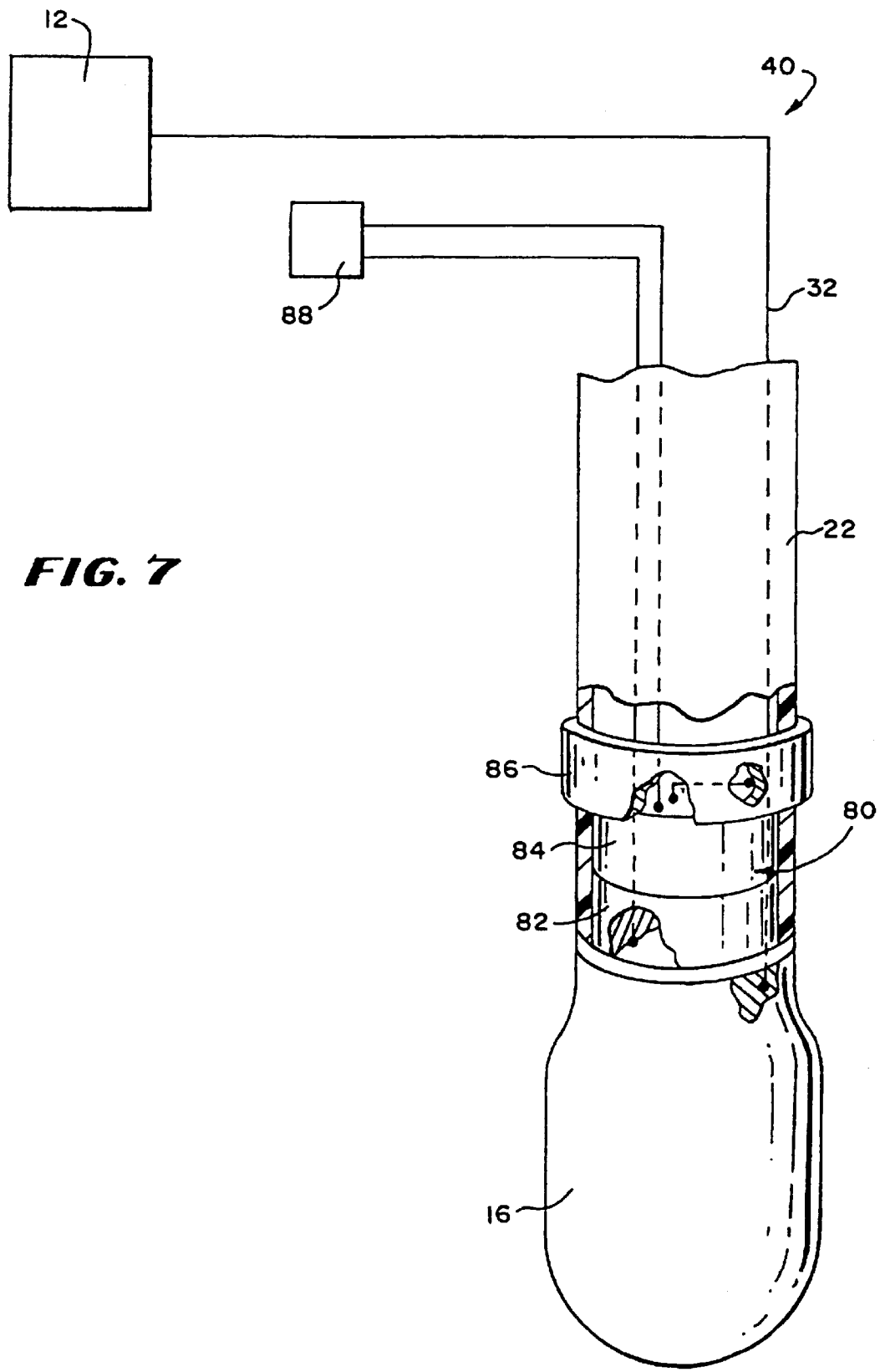
FIG. 7 is a side section view of an electrode actively cooled using a Peltier diode that can be used in the system shown in FIG. 1A.

In the alternative embodiment shown in FIG. 7, the cooling assembly 40 includes a conventional Peltier cooling diode 80 associated with the electrode 16, which is also electrically coupled by wire 32 to the generator 12. The materials of the diode 80 are complex alloys, one doped "p" and the other doped "n", like semiconductors, creating a thermocouple at the junction. An applied voltage potential passes current from a source 88 through the junction. The polarity of the voltage creates a "cold" side 82 of the diode 80, which is coupled in thermal conductive contact to the electrode 16, and a "hot" side 84 of the diode 80, which is coupled in thermal conductive contact to a heat dispersing element 86. The dispersing element 86 can be carried on the catheter body 22 away from the electrode 16 and in contact with the blood pool.

The passage of current through the diode 80 creates a heat pump from cold side 82 to hot side 84, conducting heat energy from the thermal mass of the electrode 16 to the heat dispersing element 86. Heat energy can thus be transferred from the thermal mass of the electrode 16 to cool it.

FIG. 7 shows the Peltier diode 80 being used in place of a source 50 of cooling medium to actively cool the electrode 16 in either an open or closed loop fashion. It is believed that the heat transfer capabilities of conventional Peltier diodes 50, coupled with the normal convective cooling effects of the dispersing element 86 by the blood pool can accommodate the requirements for active cooling of most ablation electrodes 16. Alternatively, the Peltier diode 80 can be used in combination with a flowing source 50 of cooling medium to actively cool the electrode.

B. Ablation Control Using Electrode Cooling

1. Prescribing a Desired Lesion Depth

Figure 8:
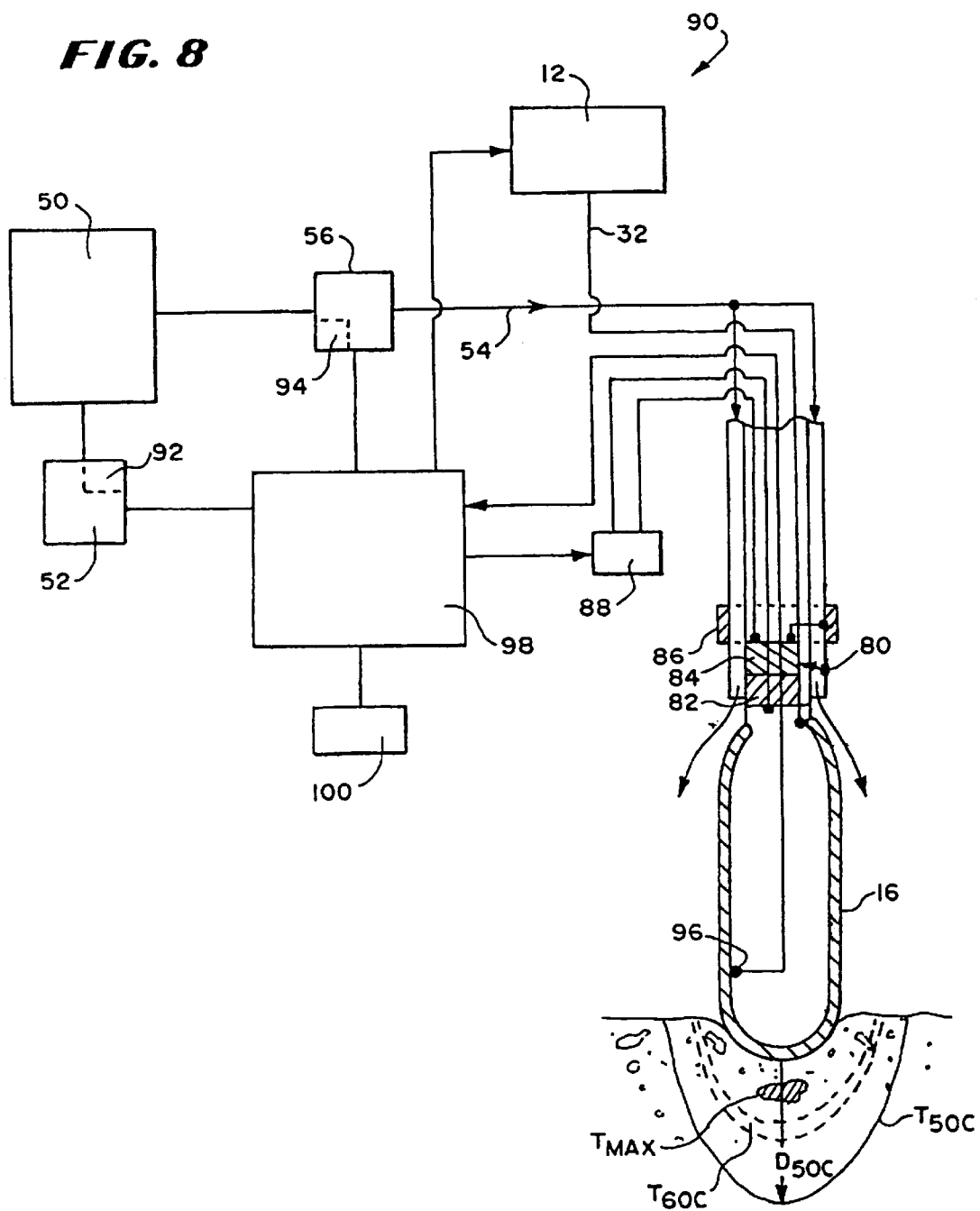
FIG. 8 is a diagrammatic view of a system for establishing a desired temperature boundary condition between an ablation electrode and endocardial tissue by actively cooling the electrode at a controlled rate.

FIG. 8 diagrammatically shows a system 90 for establishing a desired temperature boundary condition between an ablation electrode 16 and endocardial tissue by actively cooling the electrode 16 at a controlled rate.

The system 90 includes the generator 12 of RF ablation energy electrically coupled by the wire 32 to the ablation electrode 16, which is deployed within the body in contact with heart tissue. In the illustrated embodiment, when used for cardiac ablation, the generator 12 is typically conditioned to deliver up to 150 watts of power at a radio frequency of 500 kHz.

The system 90 shown in FIG. 8 also includes the source 50 of medium for cooling the electrode, as well as the mechanism 52 for cooling the medium. The mechanism 52 includes a controller 92 for establishing and maintaining a desired temperature for the cooling medium in the source.

The supply line 54 and in-line pump 56 provide communication between the source 50 and the connection port 44 on the catheter handle 20. Operation of the pump 56 conveys the cooled medium to the electrode 16, as already described. FIG. 8 shows an open loop arrangement of the type shown in FIGS. 3A/B. A controller 94 coupled to the pump 56 establishes and maintains a commanded flow rate. In a closed loop system, a return line 72 conveys the medium from the electrode for return to the source 50 or to waste 70, in the manner shown in FIG. 6.

As shown in FIG. 8, the electrode 16 carries a temperature sensor 96. The sensor 96 senses instantaneous temperatures (T1) of the thermal mass of the electrode 16. The temperature T1 at any given time is a function of the power supplied to the electrode 16 by the generator 12 and the rate at which the electrode 16 is cooled by the medium.

The characteristic of a lesion can be expressed in terms of the depth below the tissue surface of the 50° C. isothermal region $T_{50C}$, which marks the boundary of tissue rendered nonviable. FIG. 8 designates this depth as $D_{50C}$. The depth $D_{50C}$ is a function of the physical characteristics of the ablation electrode (that is, its electrical and thermal conductivities and size); the angle between the tissue and the electrode; the temperature T1 of the thermal mass of the electrode; the magnitude of RF power (P) transmitted by the electrode into the tissue, and the time (t) the tissue is exposed to the RF power. These relationships can be observed empirically and/or by computer modeling under controlled real and simulated conditions, as the following Example will illustrate.

For a desired lesion depth $D_{50C}$, additional considerations of safety constrain the selection of an optimal operating condition among the operating conditions listed in the matrix. The principal safety constraints are the maximum tissue temperature $T_{MAX}$ and maximum power level $P_{MAX}$.

The maximum temperature condition $T_{MAX}$ lies within a range of temperatures which are high enough to provide deep and wide lesions (typically between about 90° C. and 98° C.), but which are safely below about 100° C., at which tissue desiccation or tissue boiling is known to occur. It is recognized that $T_{MAX}$ will occur a distance below the electrode-tissue interface between the interface and $D_{50}$.

The maximum power level $P_{MAX}$ takes into account the physical characteristics of the electrode and the power generation capacity of the RF generator 12.

EXAMPLE
(Determining a $D_{50C}$ Function)

A 3-D finite element model is created for a cooled 8F diameter/5 mm long ablation electrode held generally perpendicular in contact with an approximately 4 cm thick rectangular slice of cardiac tissue. The tip of the electrode extends about 1.3 mm into the tissue. The overall volume is a parallelpiped 8 cm long, 4 cm wide, and 4 cm thick. The model has 8144 nodes, using hexahedral elements and a nonuniform mesh.

The current density boundary conditions are set at the electrode, so that after 120 seconds (t) the maximum tissue temperature ($T_{MAX}$) reaches about 95° C. On the outer surface of the overall volume the potential is set to zero, and the temperature is fixed at 37° C. to account for the average body temperature. At the nodes on the electrode surface the temperature is set to a value that modeled the effects of actively cooling the electrode tip. This value (T1) is varied between 4° C. and 50° C. The finite element convective boundary condition at the electrode-blood interface is set to $1.8 \times 10^{-5}$ Joule (J) per cubic millimeter ($mm^3$) second (s) Kelvin K ($J/mm^3 \cdot s \cdot K$).

COSMOS is used on a Hewlett Packard workstation to solve the electrical-thermal equations. The analysis looks at the effects of electrode cooling on lesion volume, on radio frequency power (P) required to keep $T_{MAX}$ at about 95° C., and on the distance of the hottest tissue region beneath the tissue-electrode interface. The lesion dimensions are estimated from the volume enclosed by the 50° C. isothermal surface.

Figure 21:
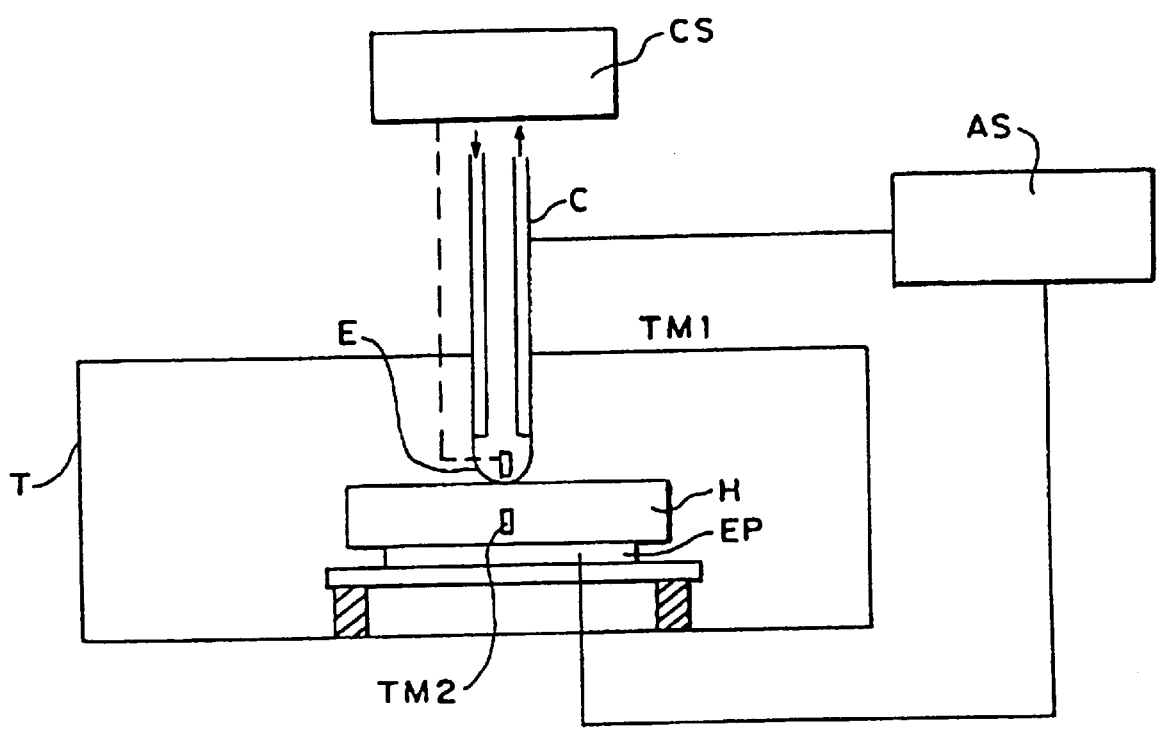
FIG. 21 is a diagrammatic view of an apparatus for acquiring experimental data to create a function that correlates a relationship among lesion boundary depth, ablation power level, ablation time, maximum tissue temperature, and electrode temperature that can be used by a processing element to control an ablation procedure to target lesion characteristics.

The model results are corroborated with experimental data acquired using the apparatus shown in FIG. 21. A 4 cm thick slice of bovine heart H is fixed in good contact with a 144 $cm^2$ patch electrode EP inside a tank T filled with saline at 37° C. An ablation catheter C carrying a cooled 8F diameter/5 mm long electrode E is placed in contact with the tissue surface H at an angle of 90°. Water at about 4° C. is circulated from a source CS inside the catheter. A 0.55 mm bead thermistor TM1 is placed at the electrode tip (to sense T1), and the sensed temperature (T1) is used as output to manually control the cooled water flow rate (as shown by dotted lines in FIG. 21). The sensed temperature (T1) is kept constant at a predetermined value between 27° C. and 40° C. A second thermistor TM2 is placed in the cardiac tissue H about 2 mm beneath the electrode tip. The second thermistor TM2 placement corresponds to the hottest tissue temperature region predicted by the finite element simulations. The two thermistor readings are acquired at a sampling rate of 20 ms by LabView running on a Power Mac IIci. A 500 kHz sinusoidal signal is applied between the ablation and indifferent electrodes using a 150 W RF ablation system AS. The delivered RF power (P) is kept constant at predetermined values between 6 watts (W) and 20 W.

After the experiments are completed, the heart is removed from the tank, sliced transversely at each of the lesions, and the dimensions of the contours marking tissue discoloration are measured. The bovine tissue used typically discolors at about 60° C., so the values obtained underestimate the dimension of in vivo lesions consisting of tissue heated above 50° C.

The following matrix sets forth the $D_{50C}$ function obtained using the above described methodology.

TABLE 1

$D_{50C}$ Boundary Function
t = 120 seconds and $T_{MAX}$ = 95° C.
(For 8F 5 mm ablation electrode)

| T1 (° C.) | $D_{50C}$ (mm) | Lesion Volume ($mm^3$) | Distance to $T_{MAX}$ (mm) | P (W) |
|---|---|---|---|---|
| 4 | 10.2 | 1.25 | 1.51 | 37 |
| 10 | 10.1 | 1.19 | 1.4 | 35.4 |
| 20 | 9.8 | 1.13 | 1.24 | 33 |
| 25 | 9.7 | 1.04 | 1.18 | 32 |
| 30 | 9.2 | 0.99 | 1.08 | 31 |
| 37 | 9 | 0.89 | 0.97 | 29.5 |
| 50 | 8.8 | 0.9 | 0.78 | 26.5 |

Other matrices can be developed using the above-described methodology for an array of values for t and $T_{MAX}$ to further define the $D_{50C}$ function.

The function in Table 1 can be further supplemented by other empirically derived information showing the cooling media flow rate needed to obtain different electrode temperatures for the particular electrode, as the following Table 2 exemplifies:

TABLE 2

Average Flow Rate of Cooling Media (Cooled Water)
vs. Electrode Temperature T1 at Constant Power Conditions
(For 8F 5 mm ablation electrode)

| T1 (° C.) | 30 | 35 | 40 |
|---|---|---|---|
| Average Flow | 9.3 ml/min | 5.3 ml/min | 4 ml/min |

The system 90 includes a master controller 98. The master controller 98 is coupled to the RF generator 12, the temperature sensor 96, the cooling controller 92, and the pump controller 94. The master controller 98 includes in memory a matrix of operating conditions defining the $D_{50C}$ temperature boundary function, as described above for t=120 seconds and $T_{MAX}$=95° C. and for an array of other operating conditions.

The master controller 98 includes an input device 100. In the system 90 shown in FIG. 8, the physician uses the controller input device 100 to set a desired lesion depth in terms of $D_{50C}$. The physician also uses the input device 100 to identify the characteristics of the electrode, using a prescribed identification code; set a desired maximum RF power level $P_{MAX}$; a desired time t; and a desired maximum tissue temperature $T_{MAX}$.

For example, assume that the physician selects an 8F/5 mm ablation electrode. The physician also selects a desired therapeutic result in terms of a lesion depth $D_{50C}$=9.2 mm. The physician further selects other details of the desired therapeutic result in terms of a targeted ablation time of t=120 seconds; a maximum tissue temperature $T_{MAX}$=95° C.; and a maximum ablation power level $P_{MAX}$=50 W.

Based upon these inputs, the master controller 98 compares the desired therapeutic result to the function defined in the matrix (as exemplified by the above Tables 1 and 2). The master controller 58 selects an operating condition to achieve the desired therapeutic result without exceeding the prescribed $T_{MAX}$ by controlling the function variables.

In this example, based upon a desired $T_{MAX}$ of 95° C. and t=120 seconds, the controller 98 commands the generator 12 to maintain a fixed power level P of 31 W (which does not exceed $P_{MAX}$) for the prescribed time t=120 seconds. The controller 98 simultaneously controls the rate at which the electrode 16 is cooled (based upon Table 2) to establish and maintain T1 at the level called for by the function for the $D_{50C}$=9.2 mm boundary selected, which in this example is T1=30° C. (flow rate=9.3 ml/min).

The maximum tissue temperature will continuously increase toward $T_{MAX}$ during the targeted ablation period t, with the rate of increase depending principally upon the magnitude of P and T1. That is, the rate of tissue temperature increase with be greater at higher values of P and lower values of T1, and vice versa.

The master controller 98 can control the cooling rate in various ways. For example, the master controller 98 can control the rate of cooling by commanding the temperature controller 92 to adjust the temperature of the cooling medium over time in response to variations in T1 to establish and maintain the set T1. Alternatively, the master controller 98 can control the rate of cooling by commanding the pump controller 94 to adjust the flow rate of the cooling medium over time in response to variations of T1 to establish and maintain the set T1. The master controller 98 can also command the controllers 92 and 94 in tandem to reach the same result.

The manner in which the master controller 98 processes information pertaining to T1 to derive control signals to vary medium temperature and medium flow rate can vary. For example, the master controller 98 can employ proportional control principles, proportional integral derivative (PID) control principles, adaptive control, neural network, and fuzzy logic control principles.

When cooling is accomplished using the Peltier cooling diode 80 (as FIG. 7 shows), the master controller 98 establishes and maintains T1 by commanding the current source 88 to adjust current flow to the diode 80. When the diode 80 is used in combination with active medium flow cooling (as FIG. 8 shows), the master controller 98 can set the medium temperature and the medium flow rate in the manners above described, and further control the current source 88 to the diode to accomplish fine adjustments to maintain the desired T1.

It can be appreciated that various combinations of cooling control using the diode 80 are also possible. As before stated, the master controller 98 can employ proportional control principles, proportional integral derivative (PID) control principles, adaptive control, neural network, and fuzzy logic control principles in varying the current flow to the diode 80 based upon changes of T1 over time.

At the end of the targeted ablation period t, the controller 98 terminates power to the ablation electrode. The desired lesion depth will be formed, and $T_{MAX}$ will not have exceeded the target of 95° C.

In alternative arrangements, the controller 98 can fix any one or more of the control variables T1, P, or t and vary the remaining one or more of the control variables T1, P, or t to achieve the desired $D_{50C}$ temperature boundary. The system 90 thereby permits the physician, in effect, to "dial-a-lesion" by specifying a desired $D_{50C}$. Using active cooling in association with time and power control, the controller 98 achieves the desired $D_{50C}$ without the need to sense actual tissue temperature conditions.

2. Predicting Maximum Tissue Temperature/Depth During cooling

Figure 9A:
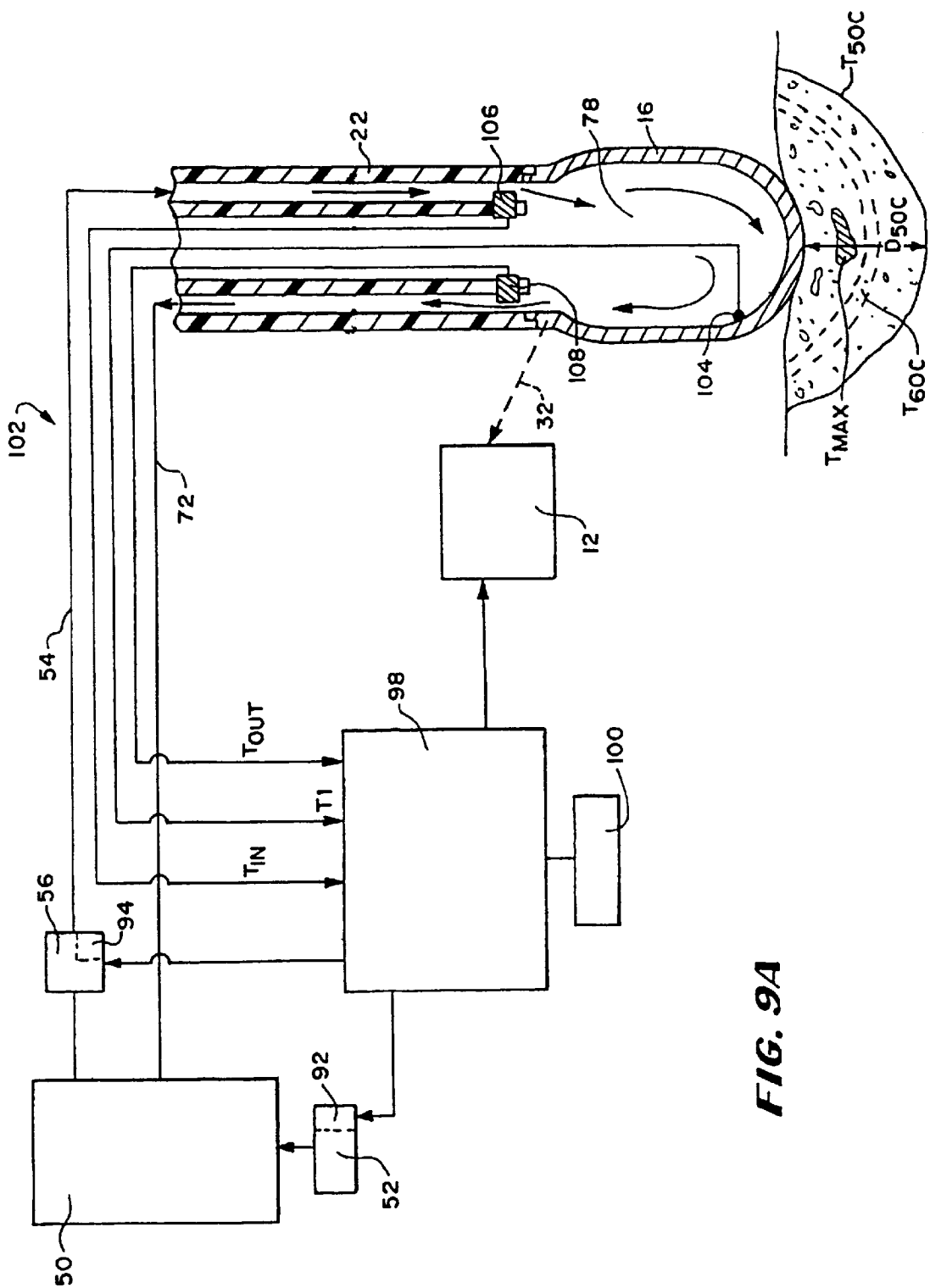
FIG. 9A is a diagrammatic view of a system that adjusts the level of RF power delivered to a cooled electrode based upon the sensed electrode temperature and the rate that ablation power is conveyed into the tissue through the cooled electrode.

FIG. 9A shows a system 102 that adjusts the level of RF power delivered to a cooled electrode 16 and/or the cooling rate based upon a prediction of instantaneous maximum tissue temperature, which is designated $T_{MAX}$ (t).

In a preferred implementation, the prediction of $T_{MAX}$ is derived by a neural network, which samples at the current time (t) a prescribed number ($k_n$) of previous power levels P, previous rates at which heat has been removed to cool the electrode, and previous electrode temperature.

The heat removal rate is identified by the expression Å, where $$Å = c \times \Delta T \times RATE$$

where:

c is the heat capacity of the cooling medium used (in Joules (J) per kilogram (kg) Kelvin (K), or J/kg K)

ΔT is the temperature drop in the cooling medium during passing through the electrode 16 (K), and RATE is the mass flow rate of the cooling medium through the electrode (kg/sec).

The heat transmitted by the ablation electrode to the tissue is the difference between the heat generated by Joule effect and the heat removed by active cooling. At a given temperature T1 and flow rate of cooling medium, the magnitude of Å increases as RF power delivered to the electrode 16 increases. Together, T1 and Å represent an indirect measurement of how rapidly the sub-surface tissue temperature is changing. Together, T1 and Å are therefore predictive of the depth and magnitude of the hottest sub-surface tissue temperature $T_{MAX}$, and thus indirectly predictive of the lesion boundary depth $D_{50C}$. Large deep lesions are predicted when T1 is maintained at a low relative temperature (by controlling cooling rate) and Å is maintained at a high relative value (by controlling RF power). Likewise, smaller lesions are predicted when T1 is maintained at a high relative temperature and Å is maintained at a low relative value.

The system 102 shown in FIG. 9A implements these control criteria using an electrode 16 of a closed system type, like that shown in FIG. 6. The electrode 16 carries three temperature sensing elements 104, 106, and 108. The first sensing element 104 is in thermal contact with the thermal mass of the electrode 16 to sense its temperature, or T1 as already described. The second sensing element 106 is located to sense the temperature of the cooling medium as it enters the electrode cavity 78, or $T_{IN}$. The third sensing element 108 is located to sense the temperature of the cooling medium as it exits the electrode cavity 78, or $T_{OUT}$. In this closed system arrangement, the temperature increase in the cooling medium during its passage through the electrode ΔT is computed as follows:

$$\Delta T = T_{OUT} - T_{IN} \qquad \text{Closed System}$$

In an open system arrangement (like that shown in FIGS. 2A/B and 3A/B), where the cooling medium is discharged directly in the region of tissue in contact with the electrode 16, there is no third temperature sensing element 108. In this case, ΔT is computed as follows:

$$\Delta T = T1 - T_{IN} \qquad \text{Open System}$$

In systems where environmental variables are closely controlled, the prediction of $T_{MAX}$ may be derived from sampling at the current time (t) a prescribed number ($k_n$) of previous power levels P and previous electrode temperatures, without sampling Å.

In FIG. 9A, the master controller 98 is coupled to the RF generator, the temperature sensing elements 104, 106, and 108 (or 104 and 106 in an open system), the cooling controller 92, and the pump controller 94.

Figure 9B:
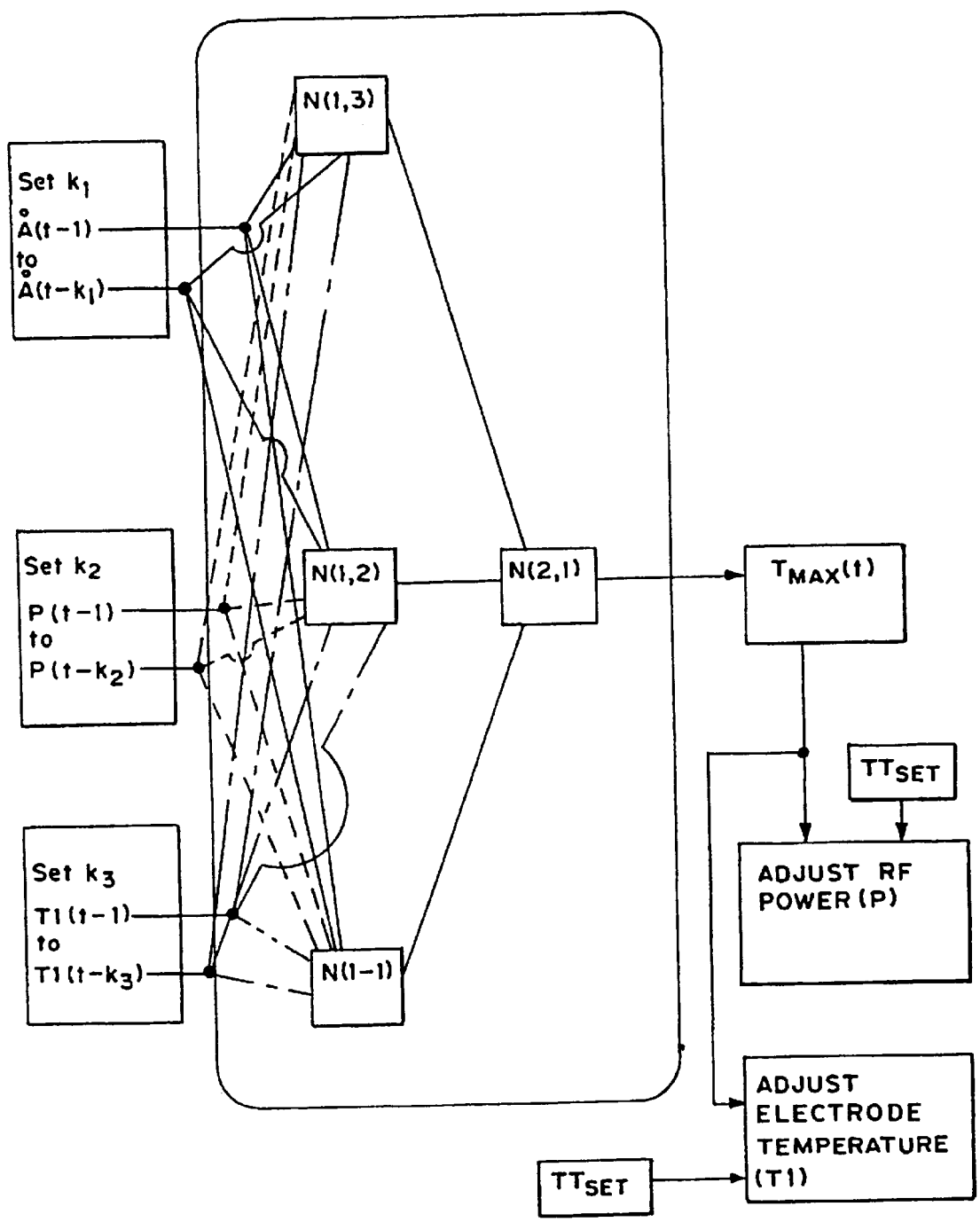
FIG. 9B is a diagrammatic view of a neural network that can be used in association with the system shown in FIG. 9A.

The controller 98 includes a neural network predictor 144 (see FIG. 9B). The predictor 144 can comprise a two-layer neural network, although more hidden layers could be used. The predictor 144 receives as inputs a first set of $k_1$ of weighted past samples of Å, {Å (t−1) to (t−$k_1$)}; a second set of $k_2$ of weighted past samples of P, {P (t−1) to (t−$k_2$)}; and a third set of $k_3$ samples of T1, {T1 (t−1) to (t−$k_3$)}. The number of samples in the sets $k_{1,2,3}$ can be varied, according to the degree of accuracy required. As an example, $k_1$ and $k_2$ are preferably in the range of 5 to 20. $k_3$ can be selected equal to 1.

The predictor 144 can be variously configured. In the illustrated embodiment, the predictor 144 comprises a two layer neural network, although more hidden layers could be used.

In this implementation, the predictor 144 includes first and second hidden layers and four neurons, designated $N_{(L,X)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprising one output neuron (X=1), designated $N_{(2,1)}$.

The weighted past samples {Å (t−1) to (t−$k_1$)}; {P (t−1) to (t−$k_2$)}; and (in the alternative embodiment) T1, {T1 (t−1) to (t−$k_3$)} are fed as inputs to each neuron $N_{(1,1)}$; $N_{(1,2)}$; and $N_{(1,3)}$ of the first layer.

The output neuron $N_{(2,1)}$ of the second layer receives as inputs the weighted outputs of the neurons $N_{(1,1)}$; $N_{(1,2)}$; and $N_{(1,3)}$. Based upon these weighted inputs, the output neuron $N_{(2,1)}$ outputs $T_{MAX}$ (t).

The predictor 144 must be trained on a known set of data that have been previously acquired experimentally. For example, using a back-propagation model, the predictor 144 can be trained to predict the known hottest temperature of the data set with the least error. Once the training phase is completed, the predictor 144 can be used to predict $T_{MAX}$ (t).

Alternatively, fuzzy logic or linear prediction algorithms can be used to derive $T_{MAX}$ (t) from sampling past power P, electrode temperature T1, and (in the preferred embodiment) cooling rate Å.

The master controller 98 receives from the physician, via the input device 100, a desired maximum tissue temperature value $TT_{SET}$, a desired electrode temperature $T1_{SET}$, and a $P_{MAX}$.

The set temperature value $TT_{SET}$ represents the desired hottest sub-surface tissue temperature that the physician wants to maintain at the ablation site, consistent with the need to prevent micro-explosions. The value $TT_{SET}$ can comprise a fixed, targeted magnitude, or the value of $TT_{SET}$ can vary over time to define a set temperature curve, which can be either linear or nonlinear. Further details of using set temperature curves are disclosed in U.S. patent application Ser. No. 08/266,023, filed Jun. 27, 1994, and entitled "Tissue Heating and Ablation Systems and Methods Using Time-Variable Set Point Temperature Curves for Monitoring and Control."

For $T1_{SET}$, the preferred embodiment takes into account the relationship between electrode temperature T1 and increases in lesion volume shown in FIG. 1D, selecting as the desired $T1_{SET}$ a temperature below about 25° C. and, most preferable, between about 10° C. and about 25° C.

The value $P_{MAX}$ is the highest allowed power level, based upon considerations already stated.

The master controller 98 periodically derives $T_{MAX}$ (t) and compares $T_{MAX}$ (t) to $TT_{SET}$ (t). Based upon this comparison, the master controller 98 derives a demand power output, taking into account $P_{MAX}$, while cooling to maintain $T1_{SET}$. The demand power output represents the magnitude of the radio frequency power that should be supplied to the electrode 16 to establish and contain the desired maximum tissue temperature $TT_{SET}$ at a fixed value or along a set linear or nonlinear curve.

Alternatively, the master controller 98 could maintain a fixed power level below $P_{MAX}$ and adjust the cooling rate Å based upon $T_{MAX}$ (t) to contain $TT_{SET}$ at a fixed value or along a set curve. As before described, the master controller 98 can control the cooling rate by commanding the temperature controller 92 to adjust the temperature of the cooling medium over time, or by commanding the pump controller 94 to adjust the flow rate of the cooling medium over time, or by commanding the controllers 92 and 94 in tandem to reach the same result.

The manner in which the controller 98 derives the control commands can vary. For example, it can employ proportional control principles, proportional integral derivative (PID) control principles, adaptive control, neural network, and fuzzy logic control principles. Further details of these control principle are disclosed in copending U.S. patent application Ser. No. 08/266,023, filed Jun. 27, 1994, and entitled "Tissue Heating and Ablation Systems and Methods Using Time-Variable Set Point Temperature Curves for Monitoring and Control."

Using active cooling in association with power control and/or rate of energy removal at the electrode, the controller 98 achieves the desired rate of energy removal Å to achieve a desired lesion characteristic. Like the system 90 shown in FIG. 8, the system 102 shown in FIG. 9A achieves its lesion formation objectives without the need to sense actual tissue temperature conditions.

Alternatively, the master controller 98 can use a matrix function to correlate observed operating conditions, which Tables 1 and 2 exemplify in partial form, to infer $T_{MAX}$ without actually sensing tissue temperature conditions.

In this implementation, the controller 98 senses the flow rate of cooling media, the sensed electrode temperature T1, and the power P. The controller 98 compares these sensed values to values set forth by in matrix function. The controller 98 infers from this comparison what $T_{MAX}$ would be, according to the function, under these sensed operating conditions. The $T_{MAX}$ inferred under this methodology becomes $T_{MAX}$. For example, at a sensed cooling flow rate of 9.3 ml/min, a sensed power P of 31 W, and a sensed electrode temperature T1 of 30° C., Tables 1 and 2 would infer that $T_{MAX}$ would be 95° C. at an ablation time (t) of 120 seconds. In this implementation the inferred maximum tissue temperature becomes $T_{MAX}$. Power and/or cooling rate are then controlled to contain $T_{MAX}$ at a fixed value or along a set curve.

3. Sensing Actual Maximum Tissue Temperature/Depth During Cooling

Figure 10:
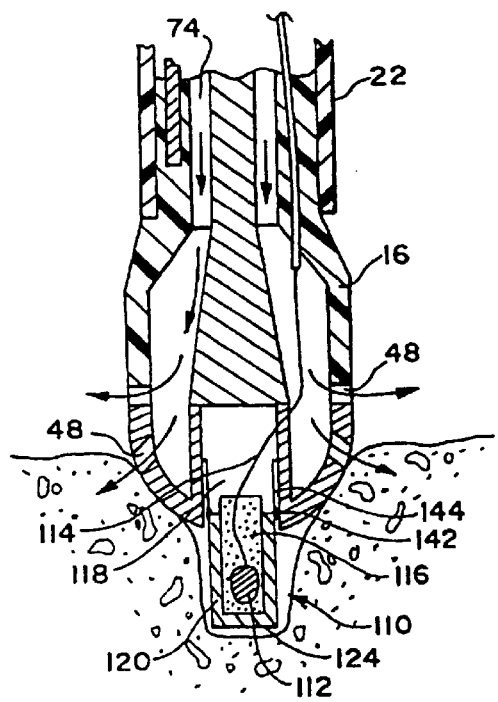
FIG. 10 is a side section view of an actively cooled energy transmitting electrode that can be associated with the system shown in FIG. 1A, showing an outward projecting, blunt end temperature sensing element carried within a heat conducting cap by the electrode for sensing tissue temperature below the tissue surface.
Figure 11:
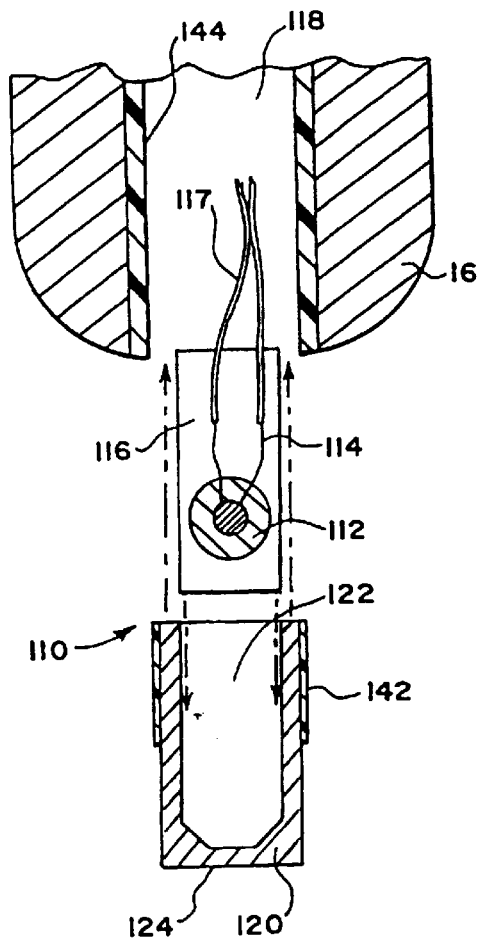
FIG. 11 is an exploded side view of the temperature sensing element shown in FIG. 10.
Figure 12:
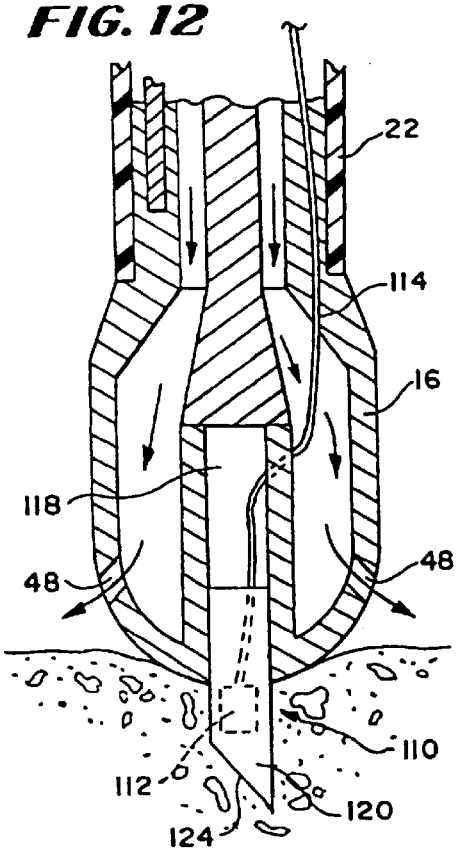
FIG. 12 is a side section view of an actively cooled energy transmitting electrode that can be associated with the system shown in FIG. 1A, showing an outward projecting, pointed end temperature sensing element carried within a heat conducting cap by the electrode for sensing tissue temperature below the tissue surface.

In the embodiments shown in FIGS. 10 to 12, the cooled ablation electrode 16 carries at least one temperature sensing element 110 for sensing actual tissue temperature. In these embodiments, the power that the RF generator 12 applies to the electrode 16 is set, at least in part, by the actual tissue temperature conditions sensed by the element 110.

In the illustrated embodiment, the temperature sensing element 110 comprises a conventional small bead thermistor 112 with associated lead wires 114. In a preferred implementation, the thermistor 42 comprises a 0.55 mm bead thermistor commercially available from Thermometrics (Edison, N.J.), Part Number AB6B2-GC16KA143E/37° C.-A.

It should be appreciated that other types of temperature sensing elements can also be used. For example, a thermocouple could be used as the temperature sensing element. In a preferred implementation, the thermocouples are constructed by either spot welding or by laser stripping and welding the different metals together to form the thermocouple junction. When a thermocouple serves as the temperature sensing element, a reference thermocouple must be used. The reference thermocouple may be placed in the handle 20 or exposed to the blood pool in the manner disclosed in copending U.S. Pat. application Ser. No. 08/286,937, filed Aug. 8, 1994, and entitled "Systems and Methods for Sensing Temperature Within the Body."

Potting compound 116 encapsulates the thermistor 112 and lead wires 114. The lead wires 114 are also enclosed in insulating sheaths 117, which electrically isolate the wires 114. Together, the compound 116 and sheaths 117 electrically insulate the thermistor 112 from the surrounding ablation electrode 16. For better performance, the wires should be electrically shielded.

The potting compound 116 and insulation sheaths 117 can be made with various materials. In the illustrated embodiment, heavy isomid serves as the potting compound 116, although another cyanoacrylate adhesive, a silicon rubber RTV adhesive, polyurethane, epoxy, or the like could be used. The sheaths 117 are made from polyamide material, although other conventional electrical insulating materials also can be used.

Similar electrical insulation is required when thermocouples are used as the temperature sensors. For example, the thermocouple junction can be placed in a thermally conducting epoxy inside a polyester sleeve. In a preferred implementation, the thermocouple junction is placed in silicon rubber RTV adhesive (NuSil Technologies, Carpenteria, Calif.) within a shrink polyester sleeve, which is then shrunk to fit tightly about the thermocouple junction and wires. To reduce electrical interference, the thermocouple wires are also preferably shielded and twisted together.

Figure 15A:
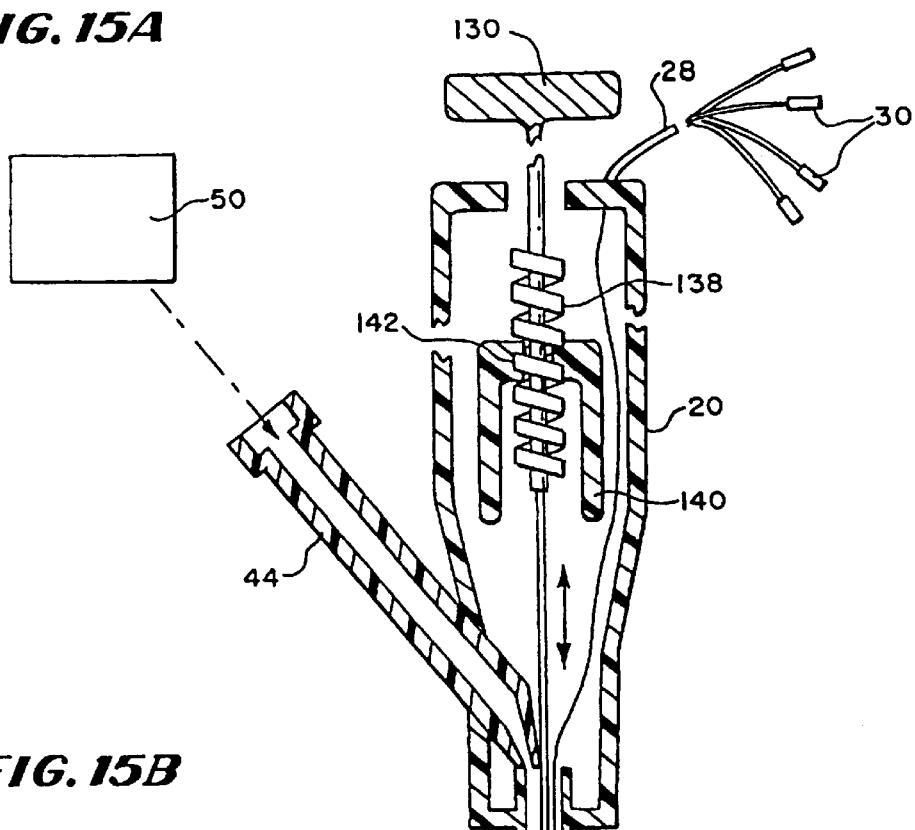
FIG. 15A is a section view of the manually rotatable stylet used to adjust the position of the movable temperature sensing element shown in FIGS. 13 and 14.

The lead wires 114 for the thermistor 112 extend through the catheter body 22 and into the catheter handle 20 (see FIG. 15A). There, the lead wires 114 electrically couple to the cable 28 extending from the handle 20. The cable 28 connects to the generator 12 and transmits the temperature signals from the thermistor 112 to the generator 12.

In the embodiment illustrated in FIGS. 10 to 12, the ablation electrode 16 includes an interior well 118 at its tip end. The temperature sensing element 110 occupies this well 118. The sensing element 110 shown in FIGS. 10 to 12 extends beyond the tip of the electrode 16 to project beneath the surface of the endocardium. The sensing element 110 is thereby positioned to sense actual sub-surface tissue temperature conditions.

In the illustrated and preferred embodiment, the sub-surface temperature sensing element 110 is enclosed within a thermally conducting cap 120 (see FIGS. 10 and 11). The cap 120 comprises a material having a high thermal conductivity that is at least 1.0 watt (W) per meter (m) Kelvin (K), or 1.0 W/m K. Metallic materials like stainless steel, gold, silver alloy, platinum, copper, nickel, titanium, and aluminum, and compositions containing stainless steel, gold, silver, platinum, copper, nickel, titanium, and aluminum possess this degree of thermal conductivity. For example, stainless steel has a thermal conductivity of about 15 W/m K, and platinum has a thermal conductivity of about 71 W/m K. This thermal conductivity is significantly higher than the thermal conductivity of conventional polymer potting material surrounding the temperature sensor 110. For example, silicon rubber has a thermal conductivity of only about 0.13 W/m K, and polyurethane has a thermal conductivity of only about 0.026 W/m K.

The cap 120 has an open interior 122. The encapsulated thermistor 112 snugly occupies the open cap interior 122 in thermal conductive contact with the thermal conducting material of the cap 120. Preferably, the thermistor 112 is potted within the open interior 122 using an epoxy having an enhanced thermal conductivity that is at least 1.0 W/m K. The inclusion of a metallic paste (for example, containing aluminum oxide) in a standard epoxy material will provide this enhanced thermal conductivity. When the ablation energy is radio frequency energy, the potting material must also electrically insulate the temperature sensing element 112 from the cap 120.

The cap 120 in turn is fitted within the well 118 of the electrode 16. The cap 120 has a distal end 124 that makes thermal conductive contact with the tissue. The high thermal conductivity of the cap material assures that the cap 120 will quickly reach an equilibrium temperature close to that of the tissue it contacts.

In a representative preferred implementation (see FIG. 3), the cap 120 is made from stainless steel 304 (having a thermal conductivity of about 15 W/m K). The cap 120 has a wall thickness along the sidewall and at the distal end of about 0.005 inch. The cap 120 has an overall length of about 0.060 inch and an overall width of about 0.033 inch (the open interior being about 0.022 inch in width). The encapsulated thermistor 42 is fixed to the cap interior 56 using a thermally conducting epoxy like EP42HTAO (Master Bond, Inc., Hackensack, N.J.). The thermal conductivity of this epoxy (with aluminum oxide) is about 1.15 W/(m K).

The cap 120 provides enhanced thermal conducting characteristics, creating an isothermal surface around the sub-surface sensing element 110 in thermal equilibrium with the surrounding tissue temperature conditions. The cap 120 also provides added strength to resist bending or fracture during manufacturing and handling.

In the illustrated and preferred embodiment, a thermal and electrically insulating barrier 142 forms an interface between the interior wall of the well 118 and the side of the cap 120 that occupies it. In a preferred embodiment, the barrier 142 comprises polyamide adhered about the sidewall of the cap 120 using FMD-14 to serve as an electrical insulator. The barrier 142 also comprises polyester shrink tubing secured by heat shrinking about the polyamide to serve as a thermal insulator.

In the illustrated and preferred embodiment, a thermal insulating tube 144 also lines the interior of the well 118. The tube 144 further thermally insulates the temperature sensing element 40 from the thermal mass of the electrode 16. In the illustrated and preferred embodiment, the thermistor-containing cap 120 and associated barrier 142 are affixed by potting within the electrode well using cyanoacrylate FMD-13 (Loctite Corporation, Newington, Conn.).

Therefore, the temperature condition sensed by the sensing element 40 within the cap 120 closely represents the actual tissue temperature condition that the cap 120 contacts.

EXAMPLE

The thermal sensitivity of a temperature sensing element enclosed in a thermally conductive carrier according to the invention (Sensor 1) was compared to the thermal sensitivity of a temperature sensing element free of the carrier (Sensor 2).

Sensor 1 was carried within the well of an 8F 4 mm standard platinum/iridium radio frequency transmitting electrode. Sensor 1 comprised a 0.55 mm bead thermistor embedded in a glass bead, which in turn was embedded in an epoxy resin, which was encapsulated in a polyamide sheath. The entire encapsulated thermistor assembly was mounted by FMD-14 within a cap, as above described, made of stainless steel 304 having a wall thickness of 0.005 inch. The exterior side walls of the cap were thermally isolated from the electrode by one layer of polyamide and one layer of polyester shrink tubing. The assembly was potted within the electrode well using FMD-13. The distal tip of the cap was free of thermal insulating material and was flush with the distal tip of the electrode for contact with tissue.

Sensor 2 comprised a thermocouple potted with solder in thermal conductive contact within an 8F/4 mm standard platinum/iridium radio frequency transmitting electrode.

The thermal sensitivity of each Sensor 1 and 2 was tested by placing the consolidated electrode and sensor assembly into a water bath maintained at 20° C. A soldering wand maintained at a temperature of 60° C. was placed into contact with each electrode beneath the surface of the water. This contact was maintained to achieve steady state conditions both against the side of the electrode (the electrode being held horizontally) and at the distal tip of the electrode (the electrode being held vertically). The temperatures sensed by each Sensors 1 and 2 in both electrode orientations were recorded.

The following Table 3 summarizes the results:

TABLE 3

Comparison of the Thermal Sensitivity of a Temperature Sensor Carried Within a Thermal Conductive Surface to the Thermal Sensitivity of a Temperature Sensor Without a Thermal Conductive Surface

|  | VERTICAL POSITION | HORIZONTAL POSITION |
|---|---|---|
| SENSOR 1 (With Thermal Conductive Surface) | 59° C. | 40° C. |
| SENSOR 2 (Without Thermal Conductive Surface) | 40° C. | 39° C. |

The above Table shows that Sensor 2 is not sensitive to the actual temperature of the 60° C. heat source. Regardless of its orientation, Sensor 2 continues to sense the 40° C. temperature of the thermal mass of the electrode itself (the remainder of the heat energy of the source being dissipated by the surrounding water bath).

In contrast, Sensor 1 shows significant sensitivity with respect to its contact orientation with the 60° C. heat source. When held horizontally, out of direct contact with the heat source, Sensor 2, like Sensor 1, senses the 40° C. temperature of the thermal mass of the electrode itself. However, when held vertically, in direct contact with the heat source, Sensor 1 essentially senses the actual temperature of the heat source, and not the temperature of the electrode. The cap encapsulating Sensor 1, having a high intrinsic thermal conductivity of at least 1.0 W/m K, directly conducts heat from the source for sensing by Sensor 1. The thermal conducting cap creates an isothermal condition about Sensor 1 close to the actual temperature of the source. Furthermore, the cap, being substantially isolated from thermal conductive contact with the electrode, retains this isothermal condition about Sensor 1, preventing its dissipation by the thermal mass of the electrode.

In quantitative terms, the 59° C. temperature sensed by Sensor 1 when in direct contact with the 60° C. heat source, compared to the 40° C. electrode temperature sensed when not in direct contact with the source, accounts for 19 of the total 20 units of actual temperature difference between the heat source and the electrode. Thus, in quantitative terms, the presence of the thermal conducting cap in Sensor 1 establishes a 95% sensitivity to the temperature of the heat source (i.e., which, in use, would be sensitivity to actual tissue temperature), and only a 5% sensitivity to the temperature of the electrode itself. This is compared to an essentially 100% sensitivity of Sensor 2 to the temperature of the electrode. In the absence of the cap that embodies the invention, Sensor 2 is virtually insensitive to the actual temperature of the heat source (i.e., actual tissue temperature).

In the embodiment shown in FIG. 10, the cap 120 presents a blunt distal end 124 that projects from the end of the electrode 16, without actually penetrating it. As FIG. 10 shows, the endocardium is malleable enough to conform about the electrode 16 and the projecting cap 120.

In the alternative embodiment shown in FIG. 12, the cap 120 presents a sharpened distal end 124 that actually penetrates the endocardium. By causing the cap 120 to actual penetrate the endocardium, better uniform tissue contact is achieved, both beneath the surface about the temperature sensing element 110 and at the surface along the electrode.

The temperature sensing element 110 can project into the tissue at any depth desired, depending upon the tissue morphology of the individual patient and the experience and judgment of the attending physician, provided, of coarse, that transmural penetration of the heart wall does not occur.

In the preferred embodiment (see FIGS. 13 and 14), the temperature sensing element 110 is movable by the physician between a retracted position within the electrode well 118 (shown in FIG. 13) and an extended position outside the electrode well 118 (shown in FIG. 14) projecting into tissue. In FIGS. 13 and 14, the temperature sensing element 110 is shown to have a blunt distal end 124, although a sensing element 110 having a sharpened distal end could also be used.

The movable nature of the temperature sensing element 110 shown in FIGS. 13 and 14 provides added protection against bending or fracture of the element until the moment of use. The element 110 can be retained in a retracted, not exposed position during handling outside the body and while being deployed to the desired site within the body.

The movement of the temperature sensing element can be accomplished in various ways. In the embodiment shown in FIGS. 13 and 14, a stylet 126 extends through the catheter body 22 within a braided protective sleeve 128 made of, for example, polyamide or stainless steel. The proximal end of the stylet 126 is attached to a control knob 130 on the handle 20 (see FIG. 15A). The distal end of the stylet 126 is secured by adhesive, solder, crimping, or the like to the cap 120.

The thermistor wires 114 extend along the outside of the stylet 126 within the protective sleeve 128 (see FIGS. 13 and 14). Another sleeve 132 of electrically insulating material, like heat shrink tubing made from Teflon® or polyester material, surrounds the stylet 126 and wires 114 up to and around the junction between the cap 120 and the stylet 126. The sleeve 132 holds the wires 114 tightly against the stylet 126. The sleeve 132 also creates a smooth transition between the stylet 126 and cap 120, while further provides protection against electrical interference. A sleeve 136 of thermally insulating material, like polyamide, also preferably lines the interior of the well, to thermally insulate the cap 120 from the thermal mass of the electrode 16.

The stylet 126 can be manually or automatically advanced in various ways. In the illustrated embodiment, the stylet 126 includes helical lands 138 formed along its length (see FIG. 15A). The lands 138 engage mating screw threads 142 within a stationary guide element 140 within the handle 20. Rotation of the control knob 130 by the physician rotates the stylet 126 within the guide element 140. Upon rotation in one direction, the helical lands 142 advance the stylet forward axially within the catheter body 22. Upon rotation in the opposite direction, the helical lands 142 move the stylet rearward axially within the catheter body 22. In this way, the sensing element 110 can be incrementally moved in a controlled fashion between the retracted and extended positions.

Figure 15B:
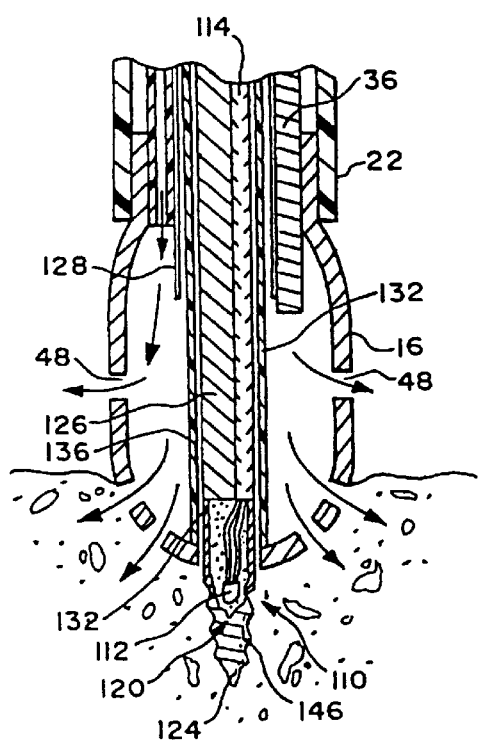
FIG. 15B is an enlarged view of an actively cooled electrode with an externally threaded, movable temperature sensing element.
Figure 15C:
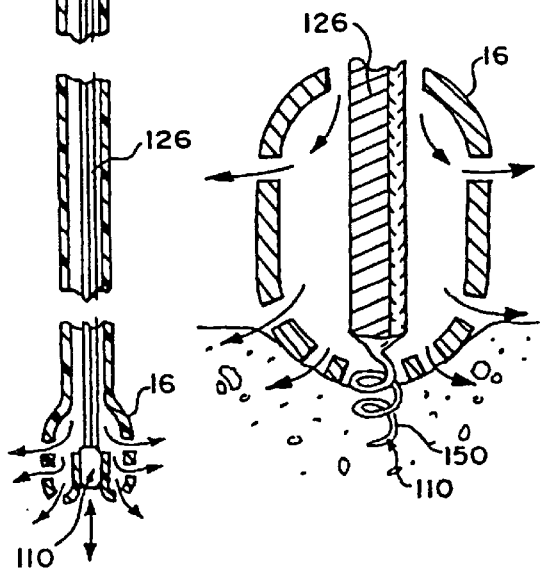
FIG. 15C is an enlarged view of an actively cooled electrode with a cork screw-type carrier for the temperature sensing element.

In this arrangement (see FIG. 15B), the distal cap end 124 can itself be threaded with helical lands 146. Upon rotational advancement of the sensing element 110 by the stylet 126, the helical lands 146 engage tissue to better anchor the element 110 for temperature sensing. Alternatively (see FIG. 15C), the stylet 126 can be attached to a carrier 150 configured as a cork-screw. Like the helical lands 146, the cork-screw carrier 150 engages tissue during rotation as the stylet 126 is advanced forward by rotation. As FIG. 15C shows, the temperature sensing element 110 is secured in thermal conductive contact with the cork-screw carrier 150 near its distal tip.

In the illustrated and preferred embodiment, the distal cap end 124 and the distal tip of the electrode 16 are marked with a fluoroscopically dense material. In this way, the travel of the temperature sensing element 110 into the tissue can be monitored by fluoroscopy as the physician incrementally advances the element 110.

Figure 16:
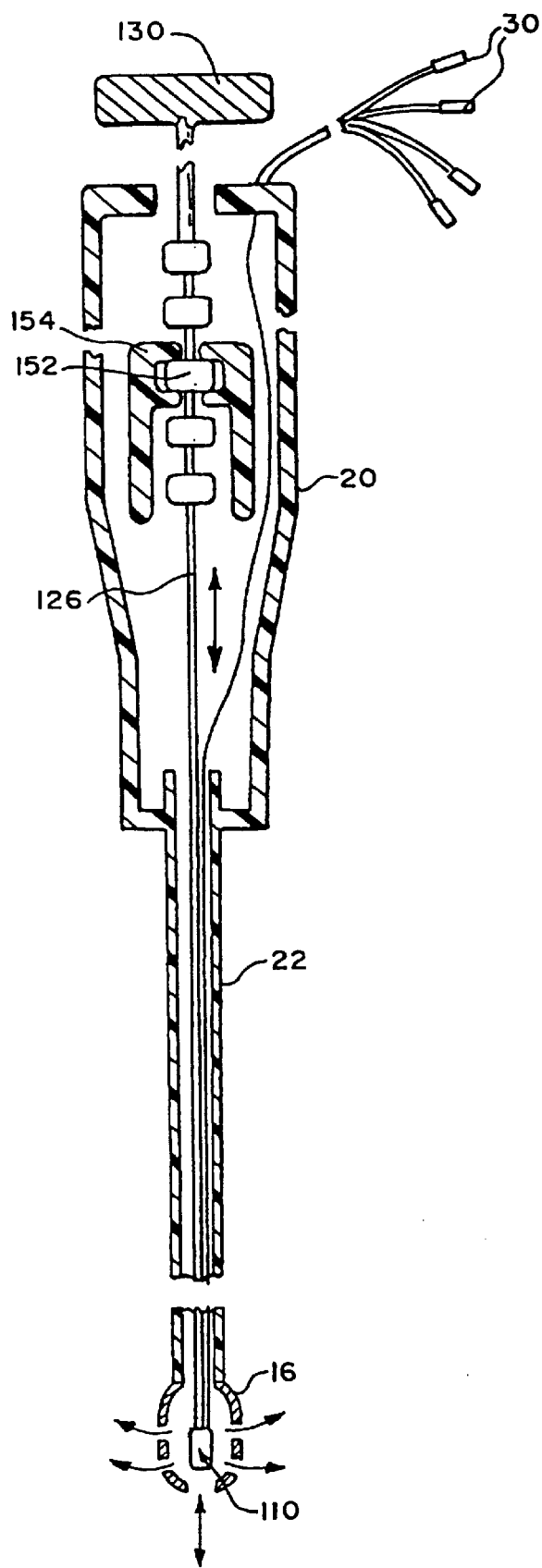
FIG. 16 is a section view of an alternative manual, push-pull type stylet used to adjust the position of the movable temperature sensing element.

Alternatively, the stylet 126 can be advanced without rotation. In this arrangement (see FIG. 16), the proximal end of the stylet 126 includes a series of ribs 152, which successively make releasable, snap-fit engagement with detent 154 in the handle 20. As the physician moves the stylet 126 in a linear (push-pull) direction, the detent 154 captures the ribs 152 one at a time, releasing the captured rib 152 in response to further linear force. Like the rotating stylet 126 shown in FIG. 8, the linear (push-pull) stylet 126 shown in FIG. 16 permits controlled, incremental movement of the sensing element 110 into and out of tissue contact.

In FIGS. 10 to 16, the actively cooled electrodes 16 shown are of the metal types shown in FIGS. 2A/B and 3A/B. It should be appreciated that a porous, actively cooled electrode body 66 like that shown in FIG. 5 can also carry a temperature sensing element 110 of a fixed or movable kind.

Figure 17A:
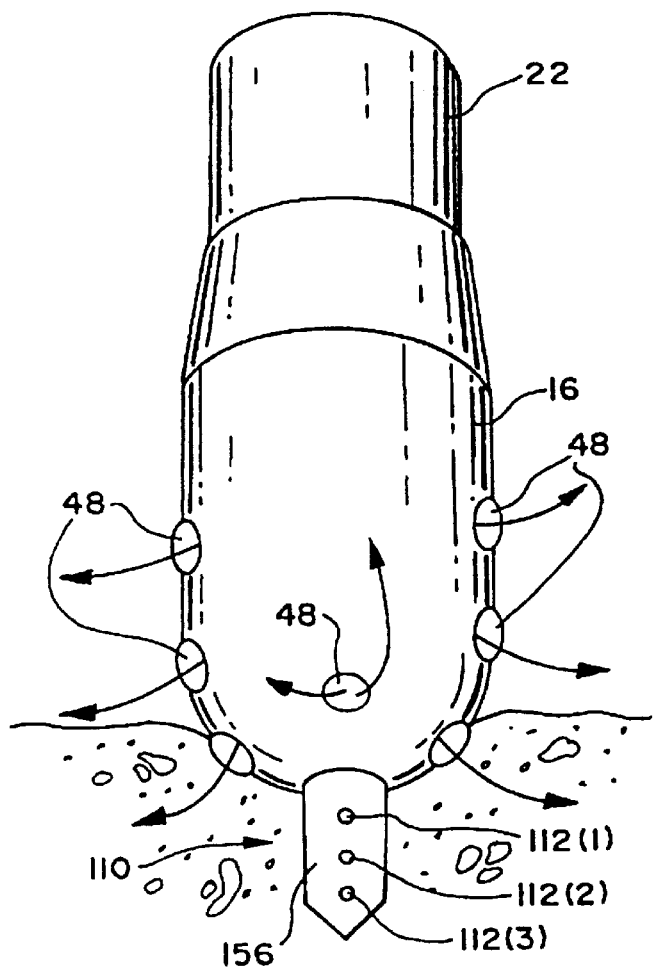
FIG. 17A is an enlarged end view of an actively cooled energy transmitting electrode carrying an outward projecting temperature sensing element with multiple temperature sensors for sensing multiple sub-surface tissue temperatures.

In another alternative embodiment shown in FIG. 17A, the actively cooled electrode 16 (which is of an open system type, having outlet apertures 48 for the cooling medium like that shown in FIGS. 2A/B) includes a temperature sensing element 110 having multiple thermocouples designated 112(1), 112(2), and 112(3). The multiple thermocouples 112(1), 112(2), and 112(3) are arranged in a housing 156 in a spaced-apart stacked relationship along the axis of the housing 156. The housing 156 can be fixed in an outwardly projecting position, as FIGS. 10 and 12, or the housing 90 can be moved into an out of the projecting position in the manner of the stylet-movable cap 120 previously described (as shown in FIGS. 13 and 14).

In one embodiment (as FIG. 17A shows), the housing 156 comprises a body formed from a conventional potting compound, like silicon rubber, RTV adhesive, polyurethane, or epoxy, having a thermal conductivity less than the tissue it contacts. In the illustrated environment, where the thermal conductivity of myocardium is about 0.43 W/m K, potting compounds like silicon rubber and polyurethane material, for example, have thermal conductivities of, respectively, 0.13 W/m K and 0.026 W/m K. The relatively low thermal capacity of this material conditions the elements 112(1)/112(2)/112(3) to sense localized relative changes in the tissue temperature gradient along the length of the housing 156. The sensing of the relative temperature gradient permits the identification along the gradient of the maximum tissue temperature region for control purposes, although the temperatures sensed by the elements 112(1)/112(2)/112(3) will not directly represent actual tissue temperatures.

Figure 17B:
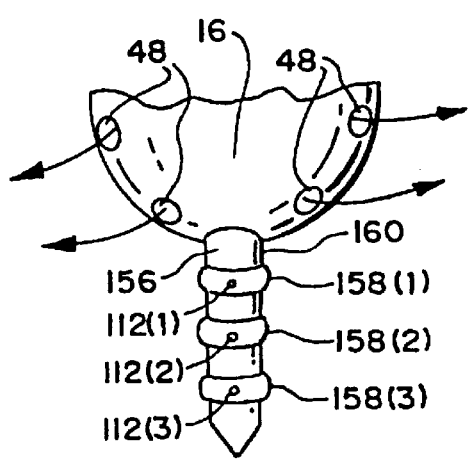
FIG. 17B is an enlarged end view of an actively cooled electrode carrying a temperature sensing element that projects into tissue having multiple temperature sensors associated with spaced regions of thermal conductive material substantially isolated from thermal conductive contact with each other.

If a more direct correspondence between sensed and actual tissue temperatures is required, the housing 156 (see FIG. 17B) can include spaced bands 158(1), 158(2), and 158(3) of thermal conductive material having thermal conductivity well above the contacted tissue, of at least 1.0 W/m K, as already described. The spaced bands 158(1), 158(2), 158(3) establish localized regions of thermal conductive contact between individual sensing element 112(1), 112(2), and 112(3) and tissue immediately adjacent to the respective band. Thermal insulating material 160 substantially isolates the spaced bands 112(1), 112(2), and 112(3) from thermal conductive contact with each another. The thermally isolated bands 112(1), 112(2), and 112(3), each with a relatively high thermal conductivity, more accurately obtain the actual tissue temperature gradient along the length of the housing 156, than when materials with lower thermal conductivities are used.

In either embodiment, the multiple, axially stacked thermocouples 112(1), 112(2), and 112(3) allow the physician to obtain and monitor a profile of temperate conditions at different depths beneath the tissue surface. The physician can manually select for ablation control purposes the one thermocouple located in the hottest sub-surface temperature region. Alternatively, an automated control mechanism can automatically compare temperatures from all thermocouples 112(1), 112(2), and 112(3) and output the hottest sub-surface temperature for temperature control purposes.

Figure 18:
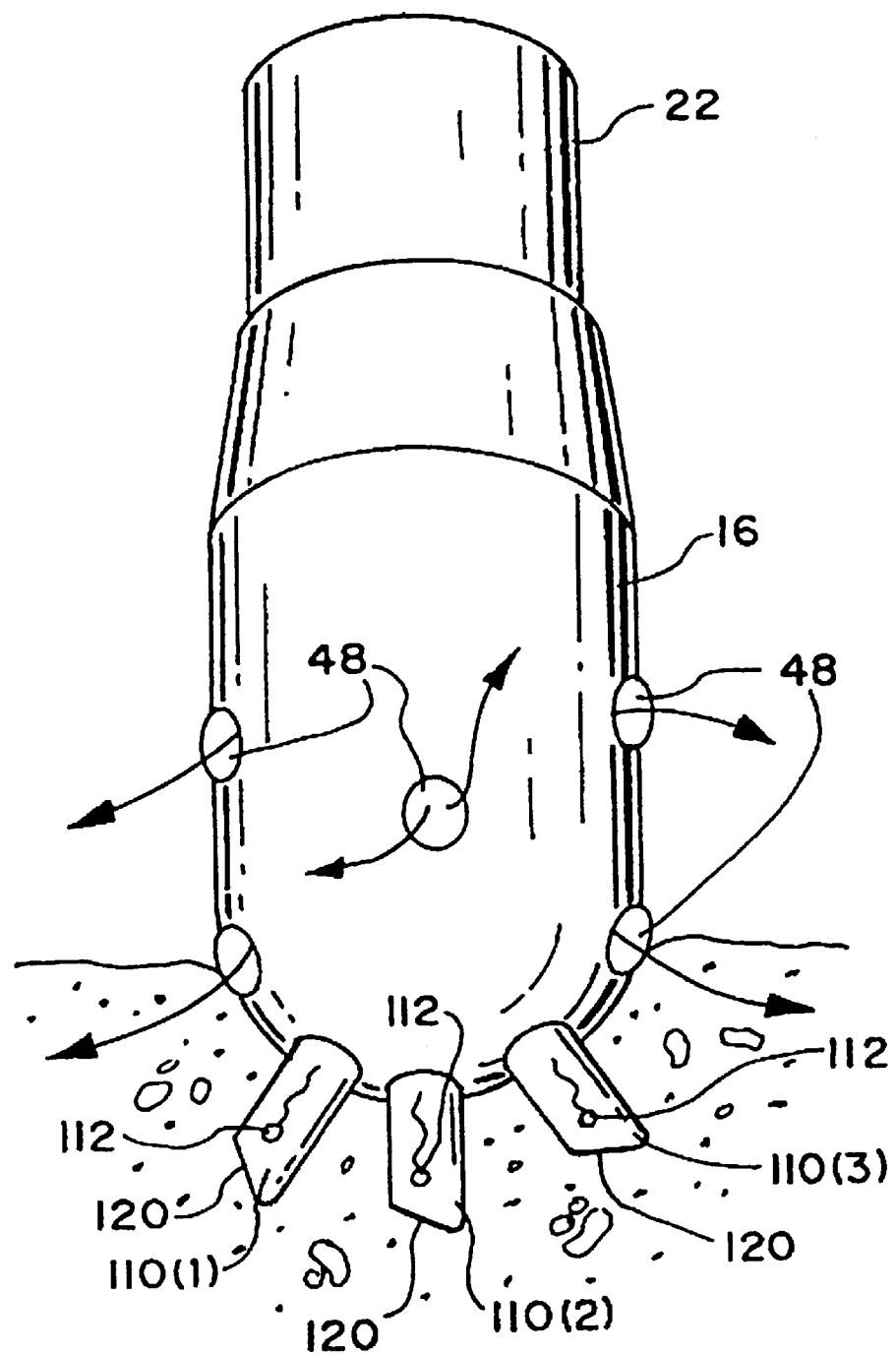
FIG. 18 is an enlarged end view of an actively cooled energy transmitting electrode carrying multiple temperature sensing elements, each sensing element projecting into tissue to sense sub-surface tissue temperature.

In the embodiment shown in FIG. 18, an array of multiple, spaced-apart temperature sensing elements (designated 110(1), 110(2), and 110(3)) project from the actively cooled electrode 16 (which is of an open system type, having outlet apertures 48 for the cooling medium like that shown in FIGS. 2A/B). Each temperature sensing element 110(1), 110(2), and 110(3) is preferably contained within an isothermal cap 120, as previously disclosed and contain a single thermistor 112 (as FIG. 18 shows), or multiple spaced-apart thermocouples (in the manner shown in FIGS. 17A/B). The array shown in FIG. 18 allows the physician to obtain and monitor a spatial map of sub-surface temperature conditions about the actively electrode 16. The physician can manually select for ablation control purposes the one sensing thermistor (or thermocouple, as the case may be) located in the hottest sub-surface temperature region. Alternatively, an automated control mechanism can automatically compare temperatures from all thermocouples 110(1), 110(2), and 110(3) and output the hottest sub-surface temperature for temperature control purposes. When the multiple-sensor array shown in FIG. 18 is used, the proper orientation of the electrode 16 generally perpendicular to the tissue surface is less critical than when single-sensor embodiments are used.

Figure 20:
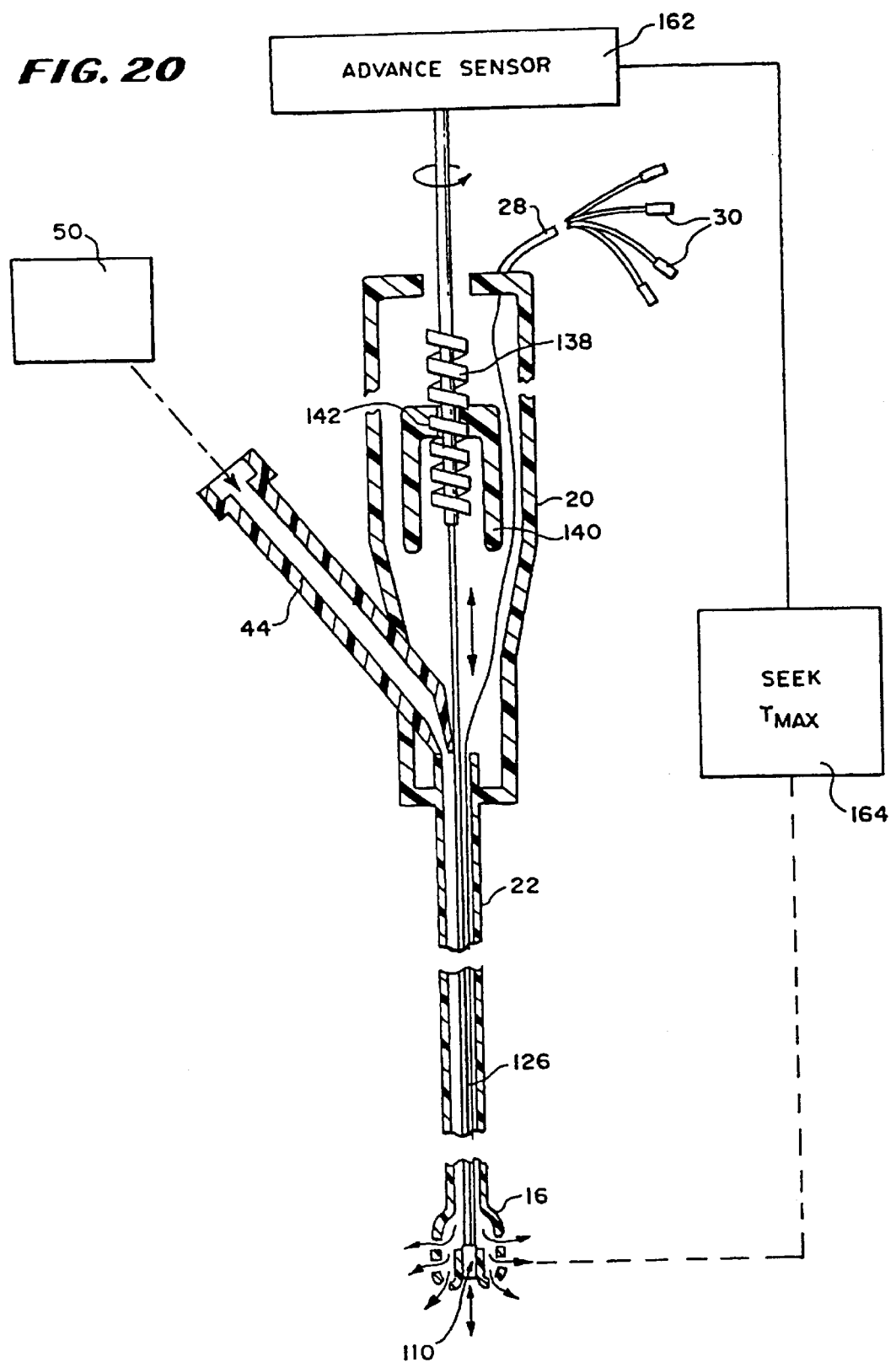
FIG. 20 is a section view of a motor driven stylet used to adjust the position of the movable temperature sensing element shown in FIGS. 13 and 14, with an associated feedback controller that seeks the region of highest sub-surface tissue temperature.

The embodiment shown in FIG. 20 includes a motor-driven mechanism 162 for advancing the stylet 126. In this embodiment, the mechanism 162 includes a feedback controller 164 electrically coupled to the temperature sensing element 110. The feedback controller 164 incrementally moves the stylet 126, while taking instantaneous measurements of temperature condition at each increment, to seek the sub-surface tissue region where the highest temperature conditions exist. The controller 164 outputs the sensed highest temperature while incrementally adjusting the position of the element 110, as necessary, to maintain it in the highest sub-surface temperature region.

Figure 22:
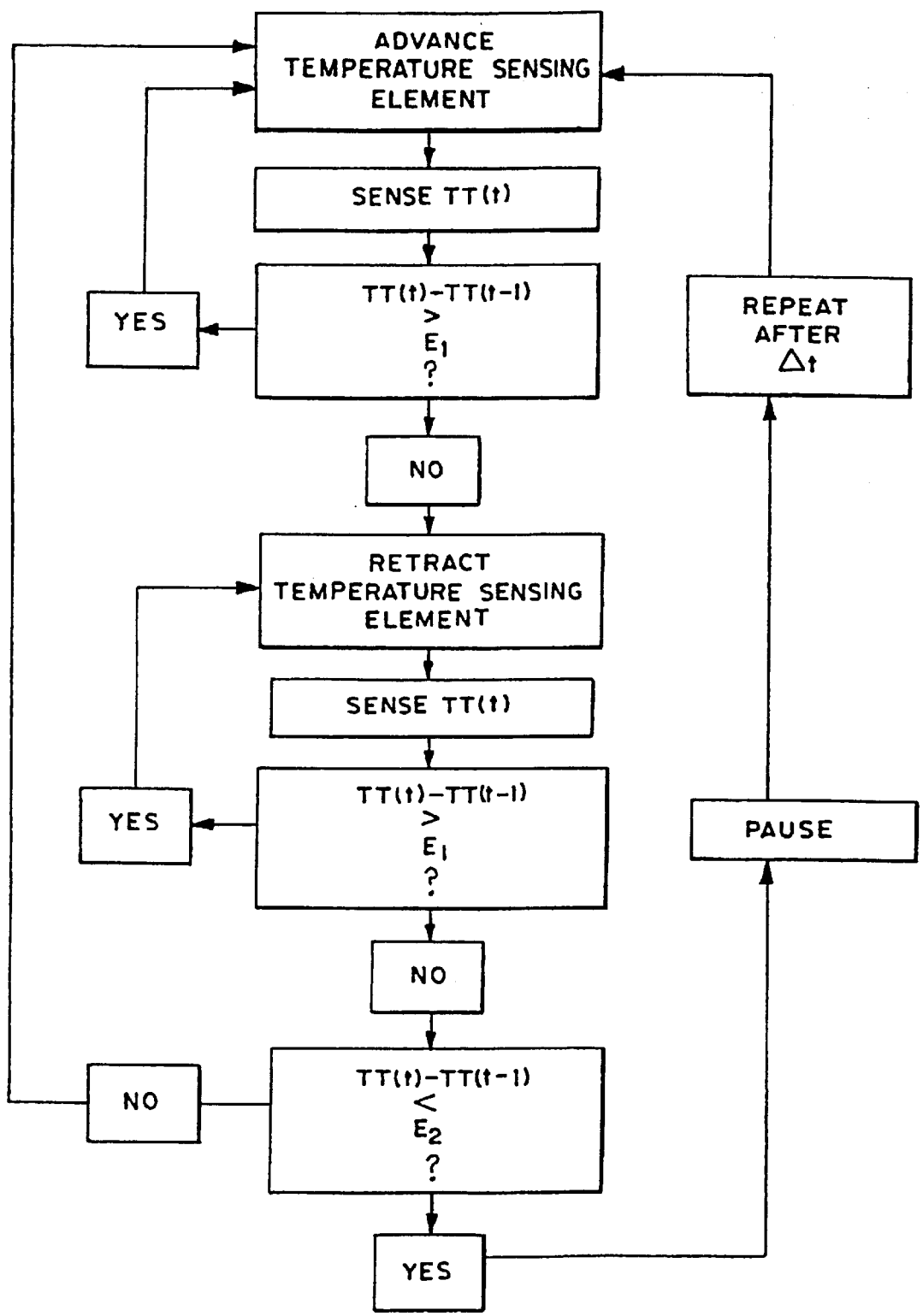
FIG. 22 is a diagrammatic flow chart showing a process that the feedback controller for the motor driven stylet shown in FIG. 20 can use to position the temperature sensor in the region of highest sub-surface tissue temperature.

Various control processes can be used to command movement of the stylet 126 to position the temperature sensing element 110 in the region of highest sub-surface tissue temperature. For example, proportional control principles, proportional integral derivative (PID) control principles, adaptive control, neural network, and fuzzy logic control principles can be used. FIG. 22 shows a representative control process 166 that the feedback controller 164 can use.

While incrementally moving the stylet 126, the process 166 inputs instantaneous tissue temperatures TT(t) sampled by the element 110 at a prescribed time interval $\Delta t$. $\Delta t$ can vary according to the degree of accuracy and sensitivity required. For example, $\Delta t$ can be 5 seconds.

The process 166 derives a temperature difference $\Delta TT$ between successive samples ($\Delta TT=TT(t)-TT(t-1)$). The process 166 employs prescribed coarse and fine differential temperature threshold values, respectively $E_1$ and $E_2$, to home in on the maximum tissue temperature. The differential threshold values can vary, again according to the accuracy and sensitivity required. For example, the coarse differential threshold value $E_1$ can be set to 5° C., and the fine differential threshold value $E_2$ can be set to 1° C.

As long as $\Delta TT$ exceeds the coarse differential threshold $E_1$, the process 166 commands incremental advancement of the stylet 126, moving the element 110 deeper into tissue. When $\Delta TT$ equals or falls below $E_1$, the process 166 begins to command incremental retraction of the style 126 and element 110, while beginning to compare $\Delta TT$ to the fine differential threshold $E_2$. The process 166 continues to command incremental retraction of the stylet 126 as long as $\Delta TT \leq E_1$, until $\Delta TT$ drops below $E_2$, at which time the process 166 commands the stylet 126 to pause for the set time interval. The process 166 then repeats the above sequence, to seek and maintain the sensor 110 at the depth where the highest tissue temperature exists.

Preferably, the process 166 also sets upper absolute limits for advancing and retracting the stylet 126 and element 110 within tissue, so that the element 110 remains within a prescribed range of depths to avoid transmural penetration (if too deep) and loss of sub-surface tissue contact (if not deep enough). Preferably, the speed of incremental advancement or retraction should be faster than the speed of the thermal wave front in the tissue.

Figure 19:
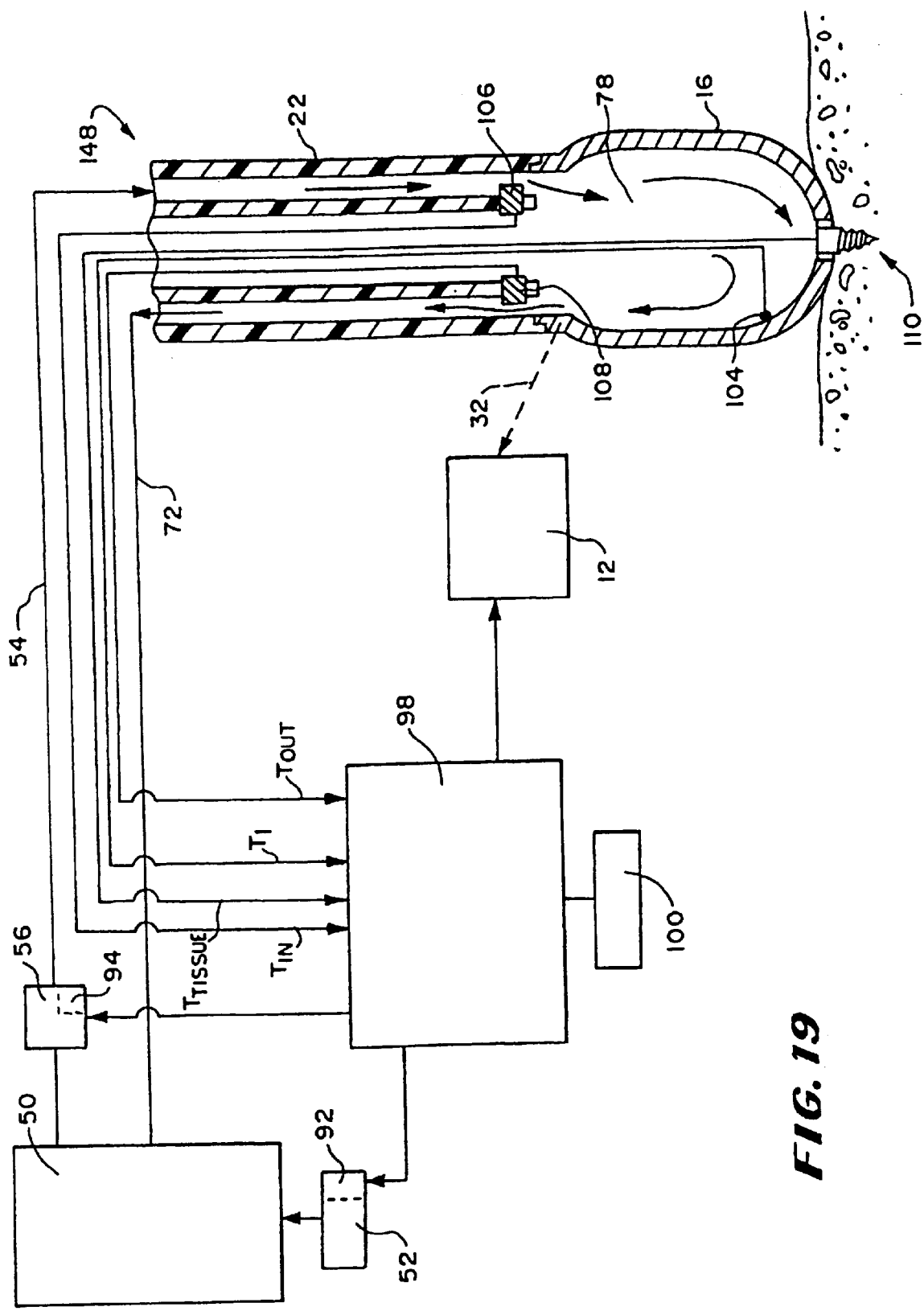
FIG. 19 is a diagrammatic view of a system that adjusts the level of RF power delivered to a cooled electrode based in part upon actual maximum sub-surface tissue temperatures sensed by a temperature sensing element that penetrates below the tissue surface.

The system 148 shown in FIG. 19 is like the system 102 shown in FIG. 9A. As in the system 102, the cooled ablation electrode 16 carries three temperature sensing elements 104, 106, and 108, for sensing T1, $T_{IN}$, and $T_{OUT}$, respectively, as already described. Unlike system 102, in the system 148, the cooled ablation electrode 16 carries at least one additional temperature sensing element 110 for sensing actual tissue temperature.

In this arrangement, the master controller 98 receives from the physician, via the input device 100, a desired tissue temperature value $TT_{SET}$, a desired electrode temperature $T1_{SET}$, and a $P_{MAX}$. As earlier disclosed, the set temperature value $TT_{SET}$ represents the desired hottest sub-surface tissue temperature that the physician wants to maintain at the ablation site, to thereby control the incidence of micro-explosions. $TT_{SET}$ can comprise a fixed value or a set linear or nonlinear curve varying tissue temperature over time.

Likewise, the value $T1_{SET}$ represents a hottest temperature for the thermal mass of the cooled ablation electrode 16, which, as earlier stated, is believed to be between about 10° C. and about 25° C.

The value $P_{MAX}$ is the highest allowed power level, also based upon considerations already stated.

The master controller 98 periodically compares the sensed maximum tissue temperature $T_{MAX}$ to $TT_{SET}$. Based upon this comparison, the master controller 98 derives a demand power output, taking into account $P_{MAX}$, while cooling to maintain $T1_{SET}$. The demand power output represents the magnitude of the radio frequency power that should be supplied to the electrode 16 to establish and maintain the desired maximum tissue temperature $TT_{SET}$.

Alternatively, the master controller 98 could maintain a fixed power level below $P_{MAX}$ and adjust the cooling rate based upon sensed $T_{MAX}$ to achieve $TT_{SET}$. As before described, the master controller 98 can control the cooling rate by commanding the temperature controller 92 to adjust the temperature of the cooling medium over time, or by commanding the pump controller 94 to adjust the flow rate of the cooling medium over time, or by commanding the controllers 92 and 94 in tandem to reach the same result.

The manner in which the controller 98 derives the control commands can vary. For example, it can employ proportional control principles, proportional integral derivative (PID) control principles, adaptive control, neural network, and fuzzy logic control principles. Further details of these control principle are disclosed in copending U.S. patent application Ser. No. 08/266,023, filed Jun. 27, 1994, and entitled "Tissue Heating and Ablation Systems and Methods Using Time-Variable Set Point Temperature Curves for Monitoring and Control."

In a preferred implementation, the controller 98 sets a value for Å based upon the magnitude of the current demand power value, as set by the sensed tissue temperature condition $T_{MAX}$. The controller then controls the cooling rate to achieve the set value for Å. In this way, the controller maximizes the benefits of cooling the electrode at the demand power value.

The illustrated and preferred embodiments envision the use of micro-processor controlled components using digital processing to analyze information and generate feedback signals. It should be appreciated that other logic control circuits using micro-switches, AND/OR gates, invertors, and the like are equivalent to the micro-processor controlled components and techniques shown in the preferred embodiments.

Various features of the invention are set forth in the following claims.

We claim:

1. A system for ablating body tissue comprising
    an electrode having a thermal mass, the electrode having a contact region for contacting a tissue surface, the electrode being adapted to be connected to a source of radio frequency energy to conduct radio frequency energy for transmission by the electrode into the tissue surface contacting the tissue contact region, the electrode including an interior well in the tissue contact region,
    a cooling element in thermal communication with the electrode and operable to cool the thermal mass of the electrode, a tissue temperature sensing assembly carried within the interior well comprising a cap made of a thermal conductive material having a thermal conductivity that is at least 1.0 W/m K, and an insulating barrier made of thermal insulating material in the interior well to substantially thermally isolate the cap from the thermal mass of the electrode, the cap having a distal end enclosing a tissue temperature sensing element in thermal conductive contact with the thermal conductive material of the cap and holding the tissue temperature sensing element in thermal conductive contact with tissue at a distance beneath the tissue surface, the thermal conductive material of the cap reaching thermal equilibrium with tissue temperature conditions without dissipation by the thermal mass of the electrode.

2. A system for ablating body tissue comprising a generator for supplying radio frequency ablation energy, an electrode having a thermal mass, the electrode having a contact region for contacting a tissue surface, the electrode and generator being coupled to conduct radio frequency energy for transmission by the electrode into the tissue surface contacting the tissue contact region, the electrode including an interior well in the tissue contact region, a cooling element in thermal communication with the electrode and operable to cool the thermal mass of the electrode, a tissue temperature sensing assembly carried within the interior well comprising a cap made of a thermal conductive material having a thermal conductivity that is at least 1.0 W/m K, and an insulating barrier made of thermal insulating material in the interior well to substantially thermally isolate the cap from the thermal mass of the electrode, the can having a distal end enclosing a tissue temperature sensing element in thermal conductive contact with the thermal conductive material of the cap and holding the tissue temperature sensing element in thermal conductive contact with tissue at a distance beneath the tissue surface, the thermal conductive material of the cap reaching thermal equilibrium with tissue temperature conditions without dissipation by the thermal mass of the electrode, and a controller coupled to the tissue temperature sensing element and the generator to control the supply of ablation energy based, at least in part, upon temperature sensed by the tissue temperature sensing element at a distance beneath the tissue surface.

3. A system for ablating body tissue comprising a generator for supplying radio frequency ablation energy, an electrode having a thermal mass, the electrode having a contact region for contacting a tissue surface, the electrode and generator being coupled to conduct radio frequency energy for transmission by the electrode into the tissue surface contacting the tissue contact region, the electrode including an interior well in the tissue contact region, a cooling element in thermal communication with the electrode and operable to cool the thermal mass of the electrode, a tissue temperature sensing assembly carried within the interior well comprising a cap made of a thermal conductive material having a thermal conductivity that is at least 1.0 W/m K, and an insulating barrier made of thermal insulating material in the interior well to substantially thermally isolate the can from the thermal mass of the electrode, the cap having a distal end enclosing a tissue temperature sensing element in thermal conductive contact with the thermal conductive material of the cap and holding the tissue temperature sensing element in thermal conductive contact with tissue at a distance beneath the tissue surface, the thermal conductive material of the cap reaching thermal equilibrium with tissue temperature conditions without dissipation by the thermal mass of the electrode, and a controller coupled to the tissue temperature sensing element and the cooling element to control the cooling element based, at least in part, upon temperature sensed by the tissue temperature sensing element at a distance beneath the tissue surface.

4. A system according to claim 1 or 2 or 3 wherein the cooling element includes a conduit for directing cooling media from a source into thermal conductive contact with the electrode.

5. A system according to claim 1 or 2 or 3 wherein the cooling element includes a Peltier diode coupled to the electrode for conducting heat energy from the electrode in response to current flow from a current source.

6. A system according to claim 1 or 2 or 3 wherein the tissue temperature sensing element comprises a thermistor.

7. A system according to claim 1 or 2 or 3 wherein the tissue temperature sensing element comprises a thermocouple.

8. A system according to claim 1 or 2 or 3 wherein the cap includes a metallic material.

9. A system according to claim 8 wherein the metallic material is substantially isolated from thermal conductive contact with the electrode.

10. A system according to claim 8 wherein the metallic material is selected from the group consisting of stainless steel, gold, silver alloy, platinum, copper, nickel, titanium, aluminum, and compositions containing stainless steel, gold, silver, platinum, copper, nickel, titanium, and aluminum.

11. A system according to claim 1 or 2 or 3 and further including a mechanism attached to the cap to selectively move the the cap in the interior well between a first position in which the distal end of the cap and the tissue temperature sensing element are withdrawn from thermal conductive contact with tissue beneath the tissue surface and a second position in which the distal end of the cap and the tissue temperature sensing element are placed into thermal conductive contact with tissue at different distances beneath the tissue surface.

12. A system according to claim 11 wherein the tissue temperature sensing element comprises a thermistor.

13. A system according to claim 11 wherein the tissue temperature sensing element comprises a thermocouple.

14. A system according to claim 11 wherein the mechanism rotates the cap in the interior well to move the cap between the first and second positions.

15. A system according to claim 11 wherein the mechanism, without rotation of the cap in the interior well, moves the cap between the first and second positions.

16. A system according to claim 1 or 2
wherein the distal end of the cap comprises a blunt surface that projects outside the interior well and into thermal conductive contact with tissue at a distance beneath the tissue surface.

17. A system according to claim 16
wherein the tissue temperature sensing element comprises a thermistor.

18. A system according to claim 16
wherein the tissue temperature sensing element comprises a thermocouple.

19. A system according to claim 1 or 2
wherein the distal end of the cap comprises a sharpened point that penetrates tissue outside the interior well and makes thermal conductive contact with tissue at a distance beneath the tissue surface.

20. A system according to claim 19
wherein the tissue temperature sensing element comprises a thermistor.

21. A system according to claim 19
wherein the tissue temperature sensing element comprises a thermocouple.

22. A system for ablating body tissue comprising
an electrode having a thermal mass, the electrode having a contact region for contacting a tissue surface, the electrode being adapted to be connected to a source of radio frequency energy to conduct radio frequency energy for transmission by the electrode into the tissue surface contacting the tissue contact region, the electrode including an interior well in the tissue contact region,
a cooling element in thermal communication with the electrode and operable to cool the thermal mass of the electrode,
at least two tissue temperature sensing elements, and
a cap carried within the interior well, made of a thermal conductive material having a thermal conductivity that is at least 1.0 W/m K, and an insulating barrier made of thermal insulating material in the interior well to substantially thermally isolate the cap from the thermal mass of the electrode, the cap having a distal end enclosing the tissue temperature sensing elements in a spaced apart relationship in thermal conductive contact with the thermal conductive material of the cap and holding the tissue temperature sensing element in thermal conductive contact with tissue at different distances beneath the tissue surface, the thermal conductive material of the cap reaching thermal equilibrium with tissue temperature conditions without dissipation by the thermal mass of the electrode.

23. A system according to claim 22
wherein the distal end of the cap comprises a blunt surface that projects outside the interior well and into thermal conductive contact with tissue at different distances beneath the tissue surface.

24. A system according to claim 22
wherein the distal end of the cap comprises a sharpened point that penetrates tissue outside the interior well and makes thermal conductive contact with tissue at different distances beneath the tissue surface.

25. A system according to claim 22
wherein at least one of the tissue temperature sensing elements comprises a thermistor.

26. A system according to claim 22
wherein at least one of the tissue temperature sensing elements comprises a thermocouple.

27. A system according to claim 22
wherein at least a portion of the cap includes a metallic material.

28. A system according to claim 27
wherein the metallic material is selected from the group consisting of stainless steel, gold, silver alloy, platinum, copper, nickel, titanium, aluminum, and compositions containing stainless steel, gold, silver, platinum, copper, nickel, titanium, and aluminum.

29. A system according to claim 22
wherein the cap includes spaced regions comprising the thermal conductive material, each spaced region being in thermal conductive contact with one of the tissue temperature sensing elements, the spaced regions being substantially isolated from thermal conductive conduct with each other and with the thermal mass of the electrode.

30. A system according to claim 29
wherein at least one of the regions includes a metallic material.

31. A system according to claim 30
wherein the metallic material is selected from the group consisting of stainless steel, gold, silver alloy, platinum, copper, nickel, titanium, aluminum, and compositions containing stainless steel, gold, silver, platinum, copper, nickel, titanium, and aluminum.

32. A system for ablating body tissue comprising
an electrode having a thermal mass, the electrode having a contact region for contacting a tissue surface, the electrode being adapted to be connected to a source of radio frequency energy to conduct radio frequency energy for transmission by the electrode into the tissue surface contacting the tissue contact region, the electrode including an interior well in the tissue contact region,
a cooling element in thermal communication with the electrode and operable to cool the thermal mass of the electrode,
at least two tissue temperature sensing elements, and
at least two spaced apart caps carried within the interior well, each cap being made of a thermal conductive material having a thermal conductivity that is at least 1.0 W/m K, and an insulating barrier made of thermal insulating material in the interior well to substantially thermally isolate each cap from the thermal mass of the electrode, each cap having a distal end enclosing at least one tissue temperature sensing element in thermal conductive contact with the thermal conductive material of the cap and holding the tissue temperature sensing element in thermal conductive contact with tissue at a distance beneath the tissue surface, the thermal conductive material of the caps reaching thermal equilibrium with tissue temperature conditions without dissipation by the thermal mass of the electrode.

33. A system according to claim 32
wherein the distal end of at least one of the caps comprises a blunt surface that projects outside the interior well and into thermal conductive contact with tissue at a distance beneath the tissue surface.

34. A system according to claim 32
wherein the distal end of at least one of the caps comprises a sharpened point that penetrates tissue outside the interior well and makes thermal conductive contact with tissue at a distance beneath the tissue surface.

35. A system according to claim 32 wherein at least one of the tissue temperature sensing elements comprises a thermistor.

36. A system according to claim 32 wherein at least one of the tissue temperature sensing elements comprises a thermocouple.

37. A system according to claim 32 wherein at least one of the caps includes a metallic material.

38. A system according to claim 37 wherein the metallic material is selected from the group consisting of stainless steel, gold, silver alloy, platinum, copper, nickel, titanium, aluminum, and compositions containing stainless steel, gold, silver, platinum, copper, nickel, titanium, and aluminum.

39. A method for ablating heart tissue comprising the steps of deploying an electrode into a heart chamber for contacting heart tissue, the electrode having a thermal mass and a contact region for contacting a tissue surface, the electrode including an interior well in the tissue contact region, conducting radio frequency energy to the electrode for transmission by the electrode into the tissue surface contacting the tissue contact region, cooling the thermal mass of the electrode at least in part while the electrode transmits radio frequency energy, enclosing a tissue temperature sensing element within a cap carried within the interior well of the electrode, the cap being made of a thermal conductive material having a thermal conductivity that is at least 1.0 W/m K, and an insulating barrier made of thermal insulating material in the interior well to substantially thermally isolate the cap from the thermal mass of the electrode, the cap having a distal end enclosing the tissue temperature sensing element in thermal conductive contact with the thermal conductive material of the cap, locating the distal end of the cap in thermal conductive contact with tissue beneath the tissue surface, and controlling either the step of conduction of radio frequency energy to the electrode or the step of cooling of the electrode or both steps based, at least in part, upon temperature sensed by the temperature sensing element.

40. A method for ablating body tissue comprising the steps of supplying radio frequency energy to an electrode having a thermal mass and a contact region for contacting a tissue surface, the electrode including an interior well in the tissue contact region, cooling the thermal mass of the electrode at least in part while the electrode transmits radio frequency energy, enclosing at least two tissue temperature sensing elements in a spaced apart relationship in a cap carried within the interior well of the electrode, the cap being made of a thermal conductive material having a thermal conductivity that is at least 1.0 W/m K, and an insulating barrier made of thermal insulating material in the interior well to substantially thermally isolate the cap from the thermal mass of the electrode, the cap having a distal end enclosing the tissue temperature sensing elements in thermal conductive contact with the thermal conductive material of the cap, locating the distal end of the cap in thermal conductive contact with tissue beneath the tissue surface, simultaneously sensing at least two tissue temperature conditions using the tissue temperature sensing elements enclosed within the cap in different tissue regions beneath the tissue surface, and controlling either the step of conduction of radio frequency energy to the electrode or the step of cooling of the electrode or both steps based, at least in part, upon temperatures sensed by the tissue temperature sensing elements.

41. A method for ablating body tissue comprising the steps of supplying radio frequency energy to an electrode having a thermal mass and a contact region for contacting a tissue surface, the electrode including an interior well in the tissue contact region, cooling the thermal mass of the electrode at least in part while the electrode transmits radio frequency energy, enclosing at least two tissue temperature sensing elements in caps carried within the interior well of the electrode, each cap being made of a thermal conductive material having a thermal conductivity that is at least 1.0 W/m K, and an insulating barrier made of thermal insulating material in the interior well to substantially thermally isolate the cap from the thermal mass of the electrode, each cap having a distal end enclosing the tissue temperature sensing elements in thermal conductive contact with the thermal conductive material of the cap, locating the distal ends of the caps in thermal conductive contact with tissue at different distances beneath the tissue surface, simultaneously sensing at least two tissue temperature conditions using the tissue temperature sensing elements enclosed in the caps in thermal conductive contact with tissue at different depths beneath the tissue surface, and controlling either the step of conduction of radio frequency energy to the electrode or the step of cooling of the electrode or both steps based, at least in part, upon temperatures sensed by the tissue temperature sensing elements.

* * * * *